US008580530B2

(12) United States Patent
Buffiere et al.

(10) Patent No.: US 8,580,530 B2
(45) Date of Patent: *Nov. 12, 2013

(54) MULTIPLE ANALYSIS OF BLOOD SAMPLES

(75) Inventors: Frederic Buffiere, Pessac (FR); Yves Raisin, Ermont (FR); Eliane Rivalin, Aigremont (FR); Amparo Sanjuan, Issy-les-Moulineaux (FR)

(73) Assignee: Bio-Rad Innovations, Marnes la Coquette (FR)

( * ) Notice: Subject to any disclaimer, the term of this patent is extended or adjusted under 35 U.S.C. 154(b) by 421 days.

This patent is subject to a terminal disclaimer.

(21) Appl. No.: 12/601,825

(22) PCT Filed: Jun. 6, 2008

(86) PCT No.: PCT/EP2008/057116
§ 371 (c)(1),
(2), (4) Date: Nov. 25, 2009

(87) PCT Pub. No.: WO2008/148886
PCT Pub. Date: Dec. 11, 2008

(65) Prior Publication Data
US 2010/0178656 A1  Jul. 15, 2010

Related U.S. Application Data

(60) Provisional application No. 60/929,052, filed on Jun. 11, 2007.

(30) Foreign Application Priority Data

Jun. 8, 2007 (FR) ...................................... 07 55624

(51) Int. Cl.
G01N 33/00 (2006.01)
G01N 33/554 (2006.01)

(52) U.S. Cl.
USPC ........ 435/7.25; 435/7.1; 435/287.2; 436/513; 436/518; 436/519; 436/520; 436/521; 436/522; 436/523; 436/526; 436/533; 436/534; 436/10; 436/63; 436/172; 436/175; 422/73; 422/82.08; 422/82.09

(58) Field of Classification Search
USPC ............ 435/5, 7.1, 7.2, 7.25, 287.2; 436/513, 436/518–523, 526, 533, 534, 10, 56, 63, 436/171, 172, 175; 422/68.1, 73, 82.08, 422/82.09
See application file for complete search history.

(56) References Cited

U.S. PATENT DOCUMENTS 5,776,711 A * 7/1998 Vyas et al. .................... 435/7.25
6,913,935 B1 * 7/2005 Thomas ........................ 436/518

(Continued)

FOREIGN PATENT DOCUMENTS

JP  2001-281248  10/2001
WO  WO 85/01354  3/1985

(Continued)

OTHER PUBLICATIONS

Everett et al. Class I HLA molecules on human erythrocytes, Quantitation and transfusion effects. Transplantation 44 (1): 123-129 (Jul. 1987).*

(Continued)

*Primary Examiner* — Gail R Gabel
(74) *Attorney, Agent, or Firm* — Saliwanchik, Lloyd & Eisenschenk

(57) ABSTRACT

The invention relates to a method for detecting a plurality of antigenic molecules carried by erythrocytes and/or a plurality of anti-erythrocyte antibodies of an individual, comprising bringing a sample into contact with distinguishable beads, on which are attached a) antibodies specific for said antigens, or b) erythrocytes, erythrocyte membrane fragments or blood group antigens.

35 Claims, 14 Drawing Sheets

(56) References Cited

U.S. PATENT DOCUMENTS

| | | |
|---|---|---|
| 7,332,349 B2 * | 2/2008 | Yang et al. .................. 435/7.24 |
| 2001/0054580 A1 | 12/2001 | Watkins et al. |
| 2003/0194818 A1 | 10/2003 | Hechinger |
| 2010/0184101 A1 * | 7/2010 | Buffiere et al. ............. 435/7.25 |

FOREIGN PATENT DOCUMENTS

| WO | WO 98/21593 | 5/1998 |
|---|---|---|
| WO | WO 99/26067 | 5/1999 |
| WO | WO 2006/100477 | 9/2006 |

OTHER PUBLICATIONS

Garratty, G. et al. "Applications of flow cytofluorometry to transfusion science" *Transfusion*, Jan. 1995, pp. 157-178, vol. 35, No. 2, XP-000983723.

Freedman, J. et al. "Applications of Flow Cytometry in Transfusion Medicine" *Transfusion Medicine Reviews*, Apr. 1995, pp. 87-109, vol. 9, No. 2, XP-005441355.

Written Opinion in International Application No. PCT/EP2008/057116, Aug. 13, 2008, pp. 1-10.

* cited by examiner

MULTIPLE ANALYSIS OF BLOOD SAMPLES

CROSS-REFERENCE TO RELATED APPLICATION

This application is the U.S. national stage application of International Patent Application No. PCT/EP2008/057116, filed Jun. 6, 2008, which claims the benefit of U.S. Provisional Patent Application No. 60/929,052, filed Jun. 11, 2007, the disclosures of which are hereby incorporated by reference in their entirety, including all figures, tables and amino acid or nucleic acid sequences.

The invention relates to the analysis of the erythrocyte group and phenotype, and also to the screening for atypical anti-erythrocyte antibodies, to the determination of the compatibility between a donor and a recipient and to the demonstration of erythrocytes coated with antibodies or with activated serum complement fractions.

Blood transfusion nowadays consists in intravenously administering preparations of red blood cell concentrates (blood cell concentrates) obtained from blood donors. When there is a blood transfusion, the primary risk is linked to the possibility of an antibody and its erythrocyte antigen being reunited in the body of the recipient (the individual transfused). There are in fact, at the surface of erythrocytes, also called red blood cells, membrane antigens, in particular blood group (or system) antigens, capable of being recognized by the immune system and of triggering an immune response with red blood cell haemolysis. The consequences of such an immunological reaction may range from inefficient transfusion with no clinical sign, to a slight clinical reaction (anxiety, shivers), serious clinical reaction (shock, haemoglobinurea, renal insufficiency) or dramatic clinical reaction (shock, disseminated intravascular haemolysis) resulting in death.

The donor's red blood cells are said to be compatible with the recipient's blood if the recipient does not have any circulating antibodies directed against an erythrocyte antigen of the donor.

Among all the antigenic variants of an erythrocyte membrane antigen constituting the blood groups, more than twenty erythrocyte antigen systems have been identified to date in humans: the ABO system with the antigens A, B and H, the Rhesus (RH) system with in particular the antigens D (the absence of the D antigen being noted d), C, E, c and e, the Kell (KEL) system with in particular the two antigens K and k, the Duffy (FY) system with in particular the antigens Fya and Fyb, the Kidd (JK) system with in particular the antigens Jka and Jkb, or alternatively other systems that are less commonly investigated in practice, such as the MNS system, the Lewis (LE) system, etc. Individuals who have the same association of erythrocyte antigens belong to the same erythrocyte blood group.

Outside of pathological situations, such as in the case of autoimmune diseases, the serum of an individual may contain two types of antibodies directed against erythrocyte antigens:
  (i) antibodies referred to as typical and directed against the antigens of the ABO system (for example, anti-A antibody in an individual of group B).
  (ii) Antibodies referred to as atypical (or immune), the presence of which in the serum or plasma is circumstantial, and which are directed more particularly against non-ABO system antigens.

The "typical" or "regular" antibodies are immunoglobulins of M and/or A isotype which are capable of agglutinating red blood cells in vitro. This phenomenon is used to determine an individual's ABO group by means of the Beth-Vincent and Simonin tests (respectively a forward or reverse grouping), the Beth-Vincent test making it possible to determine the antibodies carried by the individual's red blood cells (antigenic phenotype) and the Simonin test making it possible to carry out the complementary study, i.e. to determine the circulating anti-A and/or anti-B antibodies present in the individual's serum.

In the Beth-Vincent test, the individual's red blood cells are brought into contact with test sera, or test antibodies, each having a precise antibody specificity, directed against an antigen of the ABO system. It is therefore a red blood cell agglutination test with test sera.

In the Simonin test, also called reverse test, the individual's serum or plasma, containing the latter's circulating antibodies, is brought into contact with test red blood cells, or test erythrocytes, each belonging to a precise antigenic group of the ABO system. It is therefore a serum agglutination test with test red blood cells.

The "atypical", or "irregular", or "immune", antibodies are most commonly of G isotype, appearing when there is antigenic stimulation by foreign red blood cells, for example following immunization against one or more antigens during a blood transfusion or else during a pregnancy due to a maternal immunoreaction directed against the foetal erythrocyte antigens that do not belong to the maternal blood group, in particular at the time of the birth.

The screening for these "atypical" antibodies is called Atypical Agglutinin Screen (AAS). This test is used to detect the presence or absence, in an individual's blood, of antibodies directed against various erythrocyte antigens. For this, it is sought to demonstrate the binding of these antibodies (IgG and/or IgM) to test red blood cells, the antigens of which are known. Parallel procedures are carried out with numerous types of red blood cells, the comparison of the results making it possible to deduce the specificity or specificities of the antibodies present.

The risk associated with an immunological reaction is all the greater if this reaction involves the most immunogenic antigens, such as those of the Rhesus system (the gradient of dangerousness for this system being the following: D>E>c>e>C), and then, according to an order of decreasing immunogenicity, the K antigen of the Kell system, the Fya and Fyb antigens of the Duffy system, the Jka and Jkb antigens of the Kidd system, etc.

In practice, it is impossible to take into account all these antigens in order to perform a transfusion, otherwise one would never have the right blood group at the right moment, even less since certain antigen combinations are very rare. The standard transfusion therefore most commonly takes into account only the group in the ABO system and the Rhesus D system (Rh+ or Rh−). However, in situations where there is a risk of an atypical agglutinin appearing, a certain number of other systems are taken into account, in particular Rhesus C, c, E and e and Kell, or even other systems. For these risky situations, it will then be a case of abiding by the compatibility of the donor's blood group with that of the recipient blood, taking into account the presence or the risk of appearance of these atypical agglutinins.

Thus, in a recipient patient carrying atypical anti-erythrocyte antibodies or in a risky situation, such as, in particular, in multitransfused patients who do not have atypical anti-erythrocyte antibodies and in pregnant women, it is essential to select the erythrocyte concentrate units that will be transfused in such a way that the donor's red blood cells will have to be devoid of the antigens against which the recipient's antibodies are directed or liable to appear.

In practice in transfusion, at the current time, professionals can adopt two attitudes:

either they systematically screen for the presence of atypical antibodies in the patient's serum or plasma, and if such antibodies are present, they choose erythrocyte concentrates devoid of the antigenic structures in question (this is the case most commonly encountered in France), or they carry out a direct cross match with the donor's red blood cells in the presence of the recipient's serum or plasma, in which no agglutination and/or lysis reaction should be observed.

In clinical practice in transfusion, erythrocyte phenotyping, which corresponds to screening for and identifying the blood group antigens at the surface of the red blood cells (with the exception of the particular ABO system, where the presence of the corresponding typical antibodies is also screened for), involves both the recipient and the donor.

At the recipient and donor level, three levels of erythrocyte phenotype exist for providing the recipient with compatible erythrocyte concentrates as a function of the risky situations:

determination of the ABO grouping phenotype (or ABO grouping) and standard

Rhesus phenotype (presence or absence of the D antigen); determination of the Kell Rhesus phenotype (presence or absence of the C, E, c, e and K antigens); and determination of the extended (or broadened) phenotype, i.e. determination of the presence or absence of the antigens of the Duffy system, Fya and Fyb, of the Kidd system, Jka and Jkb, of the MNS system and of the Lewis system, and of other antigens that may also be investigated according to the nature of the risk and/or of the atypical antibody revealed in the recipient's serum.

The techniques normally used for phenotyping consist, in general, in screening for the presence or absence of the antigen being investigated, using test sera containing the appropriate antibodies. Preferably, these antibodies contained in these test sera are agglutinating in nature (IgM or IgA), thereby making it possible to obtain total or partial agglutination of the erythrocytes to be phenotyped when the latter carry the antigen corresponding to the antibody present in the test serum. Nevertheless, it is possible to use non-agglutinating test antibodies (of IgG type), their presence being demonstrated by agglutination by means of an anti-immunoglobulin ("Indirect Coombs" technique). In order to screen for and identify, in the sample of serum or plasma from the patient to be tested, anti-blood group antigen antibodies, which are typical antibodies for the ABO grouping or atypical antibodies in the case of AAS, the patient's serum or plasma is in general brought into contact with test erythrocytes (also called test red blood cells), of known antigenicity in a certain number of blood group systems (ABO, Rhesus, Kell, Duffy, Kidd, MNS, etc.)). For AAS, for which the antibodies liable to be present are rather of non-agglutinating type, the techniques used are of indirect Coombs type, by agglutination with an anti-immunoglobulin or by immunoadhesion on a solid phase and revelation with red blood cells coated with an anti-immunoglobulin, as described in patent EP 0367468.

In the case of AAS, in a first step, use is made of a panel of "screening" red blood cells (two or three red blood cells of different groups chosen so as to comprise all the antigens of importance in transfusion for detecting (but not identifying) the presence or absence of atypical antibodies). When the screening is positive, the specificity of the atypical antibody or antibodies present is then identified by means of at least one panel of "identifying" red blood cells, in general comprising 10 to 15, or even 20, different red blood cells phenotyped in the vast majority of the known blood group systems.

In the case of the cross match, the indirect Coombs technique is also used. Thus, the donor red blood cells originating from samples taken from bags that may be transfused, the recipient's serum and an anti-globulin are brought together. Such an analysis results only in the determination of the presence or absence of an antibody, and does not make it possible to determine the specificity thereof.

There exists a large number of variants of the techniques used for phenotyping or AAS in the blood transfusion field, it being possible for these techniques to be manual, on an opaline plate, in a tube or in a microplate well, or in a gel column, or completely automated by means of a robot for dispensing sample and reagent, shaker, incubator, centrifuge and automatic reader, the programmes of which are suitable for the techniques implemented.

The current techniques nevertheless have a certain number of limits.

Currently, when a blood group is determined, the final result corresponds to the cumulation of several separate results, which are not determined with the same test sample. The use of several test samples from the same patient affects the reliability of the test. In addition, it requires a large volume of blood to be taken, which may be problematic in certain patients (for example, in infants and in patients suffering from severe anaemia).

For determining the ABO group in particular, the analysis is the result of the combination and the interpretation of two types of analyses: serum analyses with plasma or serum and cell analyses using the blood cell pellet.

In the case of the atypical antibody screen, screening is generally carried out as first line, and then if the result is positive, the sample is sorted in order to identify the specificity of the antibody. These two steps delay the moment at which the result is given and can cause degradation of the samples. Furthermore, the sample volume is often found to be insufficient to continue the study (this is in particular the case with antibody mixtures), making it necessary to take a further sample from the patient. The multiplicity of these steps requires the setting up of strict follow-up procedures in order to avoid errors. Moreover, all the grouping and phenotyping tests based on the agglutination principle are impossible for certain systems (Duffy, for example), where only human antibodies of isotype G are available, the latter being incapable of directly agglutinating the red blood cells carrying the specific antigen. In this case, use is made of an additional reagent (AHG) which recognizes these human immunoglobulins and allows bridging between the antibodies bound to the red blood cells to be tested. However, this type of reagent cannot be used in the case of patients having red blood cells sensitized in vivo by antibodies (autoimmune anaemia, newborn, etc.), since there is a risk of causing a non-specific agglutination reaction (agglutination even in the absence of the antigen under consideration at the surface of the red blood cell). It is therefore impossible to provide the phenotype for this category of patients and this causes a real public health problem. This is because, in this case, the transfusing physician is obliged to transfuse red blood cells for which the maximum number of antigen markers are negative, such red blood cells not always being available in therapeutic units.

In addition, with the technologies currently available, the time required to provide an exploitable result, which often results from the combination of the results of several tests, is at least of the order of twice thirty minutes, whereas situations requiring transfusions are generally emergency situations for which it would be desirable to be able to determine the compatibility between the donor and the recipient in as short a time as possible.

SUMMARY OF THE INVENTION

The present invention solves these problems by providing a rapid and simple method that can be entirely automated and that makes it possible to carry out the grouping and phenotyping of red blood cells, the screening for atypical anti-erythrocyte antibodies, the determination of the compatibility between a donor and a recipient, and the demonstration of red blood cells coated either with antibodies or with serum complement fractions, the method preferably being carried out in a multiplex format with a single sample.

The invention thus provides an in vitro method for identifying antigenic molecules carried by erythrocytes and also anti-erythrocyte antibodies that may be present in an individual, preferably in a multiplex format, comprising bringing a sample into contact with distinguishable beads to which are attached a) antibodies specific to said antigens or b) erythrocytes, erythrocyte membrane fragments or blood group antigens, under conditions which allow the antibodies to bind to their antigens, where appropriate with activation of the serum complement fraction, without agglutination, in particular of the erythrocytes or of the distinguishable beads.

More specifically, a subject of the invention is an in vitro method for identifying antigenic molecules carried by erythrocytes and/or anti-erythrocyte antibodies of an individual, comprising
a) identifying a plurality of antigenic molecules carried by erythrocytes in a biological sample, by
   (i) bringing said sample containing erythrocytes into contact, in a single test receptacle, or in several separate test receptacles, with groups of distinguishable beads, each group of distinguishable beads carrying a given antibody, specific for an antigenic molecule carried by erythrocytes, which differs from one group of beads to the other, under conditions which allow the erythrocytes to bind to the antibodies, without agglutination, said erythrocytes being labelled before or after they have been brought into contact with said groups of beads,
   (ii) eliminating the erythrocytes which have not bound to said antibodies, and
   (iii) identifying the group of beads having bound the labelled erythrocytes, thereby allowing the identification of the antigens carried by the erythrocytes detected; and/or
b) identifying a plurality of anti-erythrocyte antibodies in a biological sample, by
   (i) bringing said sample into contact, in a single test receptacle, or in several separate test receptacles, with groups of distinguishable beads, each group of distinguishable beads carrying (1) erythrocytes, (2) erythrocyte membrane fragments or (3) blood group antigens, of known phenotype which differs from one group of beads to the other, under conditions which allow the antibodies or the activated serum complement fractions present in the sample to bind to the erythrocytes, to the erythrocyte membrane fragments or to the blood group antigens, without agglutination,
   (ii) eliminating the antibodies or activated serum complement fractions which have not bound to said erythrocytes or to said erythrocyte membrane fragments or to said blood group antigens,
   (iii) labelling the bound antibodies and/or the bound activated serum complement fractions, and
   (iv) identifying the group of beads having bound the labelled antibodies or the labelled activated serum complement fractions, thereby allowing the identification of the anti-erythrocyte antibodies present.

Preferably, mode (a) and/or mode (b) are carried out in a multiplex format, in a single receptacle. The last step a-(iii) or b-(iv) then comprises analyzing the mixture so as to identify which group of beads has bound the labelled erythrocytes, or has bound the antibodies or the activated serum complement fractions, respectively.

A subject of the invention is also a set of reagents for implementing the detection method above, comprising groups of beads, each carrying at least one particular physical parameter that can be detected, and belonging to at least two different groups, one of the groups carrying a capture antibody specific for an antigenic molecule carried by erythrocytes, and the other group carrying (1) erythrocytes, (2) an erythrocyte membrane fragment or (3) a capture antigen, which is a blood group antigen.

DETAILED DESCRIPTION OF THE INVENTION

Definitions

In the present description, the terms "erythrocyte", or "red blood cell" are used indifferently to denote the same blood cell.

The term "multiplex" means that several different antigen-antibody-type reactions are analyzed simultaneously for a single sample in a single receptacle and using a single signal-reading system.

The term "simplex" means that the antigen-antibody-type reactions are analyzed in several separate receptacles. Preferably, the analyses are nevertheless carried out simultaneously, and preferably using a single signal-reading system.

The expression "antigenic molecule carried by erythrocytes" denotes not only any erythrocyte antigen found physiologically at the surface of erythrocytes, in particular a blood group antigen, but also antigens present at the surface of erythrocytes resulting from immunological reactions due to erythrocyte antigens. In this case, the term "antigenic molecule carried by erythrocytes" comprises antibodies or activated elements of the serum complement fraction, carried by erythrocytes sensitized in vivo.

In general, the antigenic molecules carried by erythrocytes are therefore chosen from the group consisting of erythrocyte membrane antigens constituting the blood groups, activated serum complement fractions carried by erythrocytes, and antibodies present at the surface of sensitized erythrocytes. Also included are antigenic molecules adsorbed onto the erythrocytes but originating from other cell populations (in particular, Lewis antigen molecules).

The expression "anti-erythrocyte antibody" denotes any antibody which binds specifically to an antigen carried by erythrocytes. The term "labelling of the bound antibodies and/or of the bound activated serum complement fractions" is understood to mean labelling of the antibodies or activated serum complement fractions which are reversibly bound or directly embedded in the erythrocyte membrane.

The term "individual" is intended to mean any animal having a plurality of blood groups. As an animal having a plurality of blood groups, mention may, for example, be made of the dog, in which eight different blood groups have been identified to date, and the cat, which has three. Of course, the term "individual" also relates to human beings, including at the foetal stage.

The term "biological sample" is intended to mean any fraction of a body fluid or of a tissue biopsy that may contain erythrocytes or anti-erythrocyte antibodies, whether physiologically or pathologically. As a biological sample, mention may therefore be made of a blood sample, and in particular a whole blood sample or a blood cell pellet sample (or a blood bag), or any other blood preparation, but also saliva, sweat, tears, milk or urine when it contains blood. It is also possible to use a plasma or serum sample for antibody screening. To determine the antigens carried by the erythrocytes, the biological sample may consist of a blood cell pellet. The sample used in mode (a) may be identical to or different from the sample used in mode (b). When the sample is identical, modes (a) and (b) can be carried out in the same receptacle, simultaneously. The biological sample may have undergone no pretreatment.

The term "antibody" refers to any whole antibody or functional fragment of an antibody comprising or consisting of at least one antigen combination site, which allows said antibody to bind to at least one antigenic determinant of an antigenic compound. By way of example of antibody fragments, mention may be made of Fab, Fab' and F(ab')$_2$ fragments and also scFv chains (single chain variable fragment), dsFv chains (double-stranded variable fragment), etc. These functional fragments may in particular be obtained by genetic engineering.

The term "capture antigen" is intended to mean an antigenic fragment attached to a solid phase, which is able to be recognized by antibodies and to allow affinity binding with the latter. The blood group antigen attached to the beads is a blood group antigen which may be a synthetic antigen, produced by chemical process or by genetic recombination. It may also be an antigen purified from a biological sample.

The term "capture antibody" is intended to mean an antibody or a part of an antibody attached to a solid phase, which is capable of retaining at least one antigenic determinant of an antigenic compound present in a biological sample, by affinity binding.

The antibodies used as detection tools may be polyclonal or monoclonal antibodies. The production of monoclonal antibodies or of polyclonal antibodies that can be used in the context of the invention comes under conventional techniques.

The monoclonal antibodies may be obtained according to the conventional lymphocyte fusion and hybridoma culture method described by Köler and Milstein (Nature, 256, p. 495-497 (1975)). Other methods for preparing monoclonal antibodies are also known (Harlow et al. editors, Antibodies A Laboratory Manual, Cold Spring Harbor Laboratory (1988)). The monoclonal antibodies may be prepared by immunizing a mammal (for example, a mouse, a rat, a rabbit or even a human being, etc.) and by using the technique of lymphocyte fusion producing hybridomas (Köler and Milstein, 1975, above).

Alternative techniques to this customary technique exist. Monoclonal antibodies can, for example, be produced by expression of a nucleic acid cloned from a hybridoma. Antibodies can also be produced by the phage display technique, by introducing antibody cDNAs into vectors, which are typically filamentous phages (for example, fUSE5 for *E. coli*, Scott et al. (Science, 249, pp. 386-390 (1990)). The latter constitute libraries and have scFv fragments at their surface. Protocols for constructing these antibody libraries are described in Marks et al. (1991) (J. Mol. Biol., 222, pp. 581-597, (1991)). The polyclonal antibodies can be obtained from the serum of an animal immunized against an antigen, preferably of peptide nature, according to the usual procedures. In general, a polypeptide, in particular a recombined polypeptide, or an oligopeptide can be used, for example, as immunogen. According to a conventional protocol, rabbits are immunized with the equivalent of 1 mg of the peptide immunogen, according to the procedure described by Benoit et al. [PNAS USA, 79, pp. 917-921 (1982)].

Beads:

The beads generally consist of polymers that are inert with respect to the constituents of the biological samples; they are solid and insoluble in the samples. The polymers used may be polyesters, polyethers, polyolefins, polyamides, polysaccharides, polyurethanes or celluloses. Binders may also be used to give the particles integrity and structure. Functional groups may be incorporated with these polymers so as to allow the attachment or the coupling of macromolecules of biological interest (proteins, lipids, carbohydrates, nucleic acids). These functional groups, which are known to those skilled in the art, may be amine (—NH2) or ammonium (—NH$_3^+$ or —NR$_3^+$) functions, alcoholic functions (—OH), carboxylic functions (—COOH) or isocyanate functions (—NCO). The monomers most commonly used for introducing COOH functions into polyolefins are acrylic acid or methacrylic acid.

The attachment of reagents to the surface of the beads can be carried out by electrostatic attractions, affinity interactions, hydrophobic interactions or covalent coupling. Covalent coupling is preferred.

The beads used in the invention are particles approximately spherical in shape, of sizes that may be between 0.5 and 40 µm, preferably between 4 and 9, and more particularly between 5 and 8 µm.

The beads used here are "distinguishable" in that they have differential markers which make it possible to distinguish them from one another by means of an appropriate detector. Each group of beads therefore has different physicochemical properties (size, density, particle size, roughness, absorbence, fluorescence, paramagnetic components) which make it possible to differentiate them from one another by means of suitable detectors or tools, for example a flow cytometer.

As a differential parameter for distinguishing the particles from one another, use may in particular be made of the size of the particles, by choosing non-overlapping size ranges.

In another preferred embodiment, the distinguishable particles emit fluorescence signals. The beads which incorporate various fluorescent labels can in fact be distinguished by their fluorescence spectrum. For this, the beads can be impregnated with one or more dyes (for example, fluorescent, luminescent, etc.), where appropriate at various concentrations, or with a label of radioisotope type, enzyme type, etc. (Venkatasubbarao S. <<Microarrays-Status and prospects>> Trends in Biotechnology December 2004, 22(12):630-637; Morgan et al, <<Cytometric bead array: a multiplexed assay platform with applications in various areas of biology>>, Clin. Immunol. (2004) 100:252-266). Scattering or emission of light, or a combination thereof, can also be used to distinguish between the particles.

In a preferred embodiment, the distinguishable beads emit luminescent or fluorescent signals.

The beads used may be superparamagnetic, magnetic or magnetizable. As beads that can be used according to the invention, mention may in particular be made of those described in U.S. Pat. No. 6,872,578. According to a particularly preferred embodiment, the beads used are fluorescent and superparamagnetic. These physicochemical properties may make it possible, during the reaction with the biological sample, to separate the fractions captured by these microparticles from those which are not bound. This separation can be carried out, inter alia, by centrifugation, filtration or magnetization. Separation by magnetization is preferred, and for this, beads containing paramagnetic, ferromagnetic, ferrimagnetic and metamagnetic components may be used. Paramagnetic components are preferred, for instance iron, cobalt, nickel or metal oxides such as $Mn_2O_3$, $Cr_2O$ or $Fe_3O_4$. The amount of magnetic components may be between (by weight) 2% and 50%, and preferably between 3% and 25%.

The antibodies may be attached to the beads (according to a) by any appropriate technique. They may be attached by direct covalence, or noncovalently, in particular by passive adsorption or by affinity. The direct covalent attachment may be carried out by means of activation of the carboxylic groups present at the surface of the beads, involving bonding via hydroxysuccinimide or carbodiimide, for example. In a specific embodiment, anti-immunoglobulin antibodies are first attached to the beads, by covalence, and then the beads are brought into contact with the antibodies to be attached.

The erythrocytes, the erythrocyte membrane fragments or the blood group antigens can be attached to the beads by noncovalent bonding via a poly-L-lysine, or by means of any type of ligand such as polycations of dye type. The erythrocytes, the erythrocyte membrane fragments or the synthetic antigens can also be attached to the beads by covalent bonding, in particular using sodium periodate.

It has been noted, surprisingly, that the attachment of the red blood cells or of the membrane fragments, whether covalent or noncovalent, does not impair the property that the beads have of being distinguishable according to a flow cytometry process.

Moreover, it is possible to attach to the surface of these beads, in the same manner, synthetic antigens that are homologues of certain blood group antigens present at the surface of erythrocytes. The attachment of these antigens does not impair the property that the beads have of being distinguishable either. Such synthetic antigens may, for example, be polysaccharides.

The beads are subjected to measurement by a detector such as a flow cytometer, as described, for example, in Luminex patent application WO 97/14028. Thus, subgroups of beads carrying a reactant (antibody or erythrocyte or erythrocyte membrane) are exposed to a biological sample, each subgroup having one or more classification parameters which make it possible to distinguish the beads of one subgroup from those of another subgroup. The beads thus exposed to the sample then go through an examination zone (for example a flow cytometer), where the data relating to the classification parameters (for example, the fluorescence emission intensities) are collected, and preferably also the data relating to the presence or absence of a complex formed between the reactant and the analyte of interest (namely between the bead and the antigenic molecule carried by the erythrocyte according to (a) or the antibody according to (b) in the method of the invention).

Labelling:

The detectably labelled erythrocytes (in mode (a)) can be labelled by any technique known to those skilled in the art. They may, for example, be labelled with a fluorescent compound, for example a fluorophore which is inserted into the membrane of these cells.

They may also be labelled using a ligand which is itself functionalized with a fluorescent label, this ligand being capable of recognizing structures at the surface of the erythrocytes. These ligands may, for example, be antibodies or animal or plant lectins. These types of labelling may or may not be carried out prior to the test.

In mode b), it is the antibodies which are labelled, alternatively it is the activated serum complement fractions. Any labelling technique is possible. The types of labelling can also be mixed.

According to a specific embodiment, the antibodies are brought into contact with an anti-human immuno globulin antibody carrying a fluorescent, luminescent or radioactive label.

According to another specific, optionally cumulative, embodiment, the activated serum fractions are brought into contact with an antibody which specifically recognizes the activated serum complement fractions said antibody carrying, for example, a fluorescent, luminescent or radioactive label. Such antibodies may be monoclonal or polyclonal and are well known to those skilled in the art.

Elimination of the Unbound Reagents:

Before carrying out the analysis step, the reagents which have not bound during the bringing into contact and the incubation of the reagents should be eliminated. It is desirable to eliminate as much unbound reagent as possible in order to reduce the background noise and therefore to obtain good specificity of the test, but conditions that are too drastic could reduce the sensitivity of said test. A residual presence of unbound reagents is therefore generally tolerable. The conditions for obtaining an acceptable compromise between the sensitivity and the specificity of the method can be readily determined by those skilled in the art by means of routine experiments.

The elimination of the unbound reagents can be carried out by any technique known to those skilled in the art, such as washing by means of repeated centrifugation steps or the use of the superparamagnetic nature of the beads and use of a magnet.

Preferred Embodiments

As defined above, the method according to the invention makes it possible either to identify the antigens according to (a), or to identify the antibodies, or else to identify the activated serum complement fractions that are bound. It also makes it possible to use combinations of several types of identification. Thus, the identification of the antigens according to (a) and the identification of the antibodies according to (b) can be carried out simultaneously or separately. The identification of the antibodies according to (b) can be carried out by revealing both the antibodies and the activated serum complement fractions.

The receptacle may be any solid container, for example a test tube, a microplate well or any receptacle that allows reactions in an automated system. It is not necessary to centrifuge the receptacles.

The mixing of the reactants and of the analyte of interest is carried out under conditions (in particular of pH, temperature, ionic strength, etc.) which allow specific binding of the antigens carried by the erythrocytes, to the antibodies, without agglutination. The substantial absence of agglutination makes it possible to use in particular a flow cytometer. In order to avoid any agglutination reaction, it is advantageous to adjust the amount and the size of the beads, and also the concentration of the sample. The agglutination reactions satisfy mathematical laws which have in particular been described by H. E. Hart, Bulletin of mathematical biology, vol 42, 17-36, by K. C. Chak, Bulletin of mathematical biology, vol 42, 37-56 and by C. DeLisi, Journal of Theoretical Biology, 1974, vol 45, pages 555-575. These laws involve several parameters such as, in particular, the size of the reagents and also their ratio by number. Those skilled in the art will therefore choose the reaction conditions by applying these mathematical laws as a function of the reagents that they use, such that no substantial agglutination occurs. For example, when erythrocytes and beads of size similar to those of the erythrocytes, i.e. of the order of 7 μm, are used, those skilled in the art will choose a ratio of the number of erythrocytes to the number of beads ranging from 30 to 150.

Advantageously, it is preferable to provide for a step of chemical or enzymatic degradation of the haemoglobin, such as a haemolysis, preferably after the attachment and before the identification of the antigens (according to a) or of the antibodies (according to b).

The haemolysis can be carried out in various ways. For example, the mixture can be incubated in a medium of low osmolarity. The term "medium of low osmolarity" is intended to mean in general a medium having an osmolarity of less than or equal to 100 mosmol/L. As suitable medium of low osmolarity, mention may be made of ammonium chloride solutions having a concentration of 40 mM or less, or distilled water. The haemolysis may also be carried out by sonication.

Applications:

The method makes it possible to carry out erythrocyte phenotyping and/or grouping, in a multiplex format.

The antigens identified by embodiment (a) of the method according to the invention may be any blood group antigen, i.e. of the ABO system with the A antigen, the B antigen, the A and B antigens expressed simultaneously or the H antigen, of the Rhesus system with the D, E, e, and C or c antigens, of the Kell system with the K or k antigen, of the Duffy system (Fya, Fyb), of the Kidd system (Jka, Jkb) or else of other systems that are less commonly investigated in practice but that also exist, such as MNS, Lewis, etc. Embodiment (a) of the method of the invention also offers the possibility of identifying the phenotype using a biological sample which comes from a patient having erythrocytes sensitized in vivo by antibodies or else by serum complement fractions. These patients are said to be "direct Coombs test-positive". They are in particular newborns or patients suffering from haemolytic anaemia for example. The fact that the red blood cells of these patients are coated with type G immunoglobulins prohibits the use of reagents that mean the involvement of an anti-human globulin secondary reagent. The indirect Coombs test cannot therefore be used in such a case. This particularity greatly limits the capacity of biologists to establish the complete phenotype of this type of patient. In fact, many phenotyping reagents exist only in the form of a solution of specific human antibodies of IgG type and require the use of an anti-human globulin secondary reagent. In certain cases, it is therefore impossible to carry out the analysis, and therefore impossible to transfuse the patient, which may, of course, affect the quality of the therapeutic procedure. To the contrary, the method according to the invention does not require the use of anti-globulin secondary reagents and therefore allows the identification of erythrocyte antigens of erythrocytes sensitized in vivo.

The antibodies or activated serum complement fractions present at the surface of erythrocytes sensitized in vivo are themselves capable of constituting antigens carried by erythrocytes that can be identified with embodiment (a) of the method according to the invention.

Advantageously, the method of the invention also makes it possible to determine the isotype of the immunoglobulins present at the surface of the erythrocytes. Since certain isotypes are more dangerous than others, it is advantageous to be able to specify the nature of the antibodies found, thus allowing the clinician to direct his or her therapeutic procedure. Thus, according to embodiment b, by using labels for antibodies specific for immunoglobulin isotypes, the isotype of the atypical antibody can be determined.

Embodiment (a) of the method according to the invention also makes it possible to reveal multiple populations of red blood cells, i.e. red blood cells of different phenotypes (double-population), sometimes encountered in multitransfused patients when they have undergone multiple blood transfusions not perfectly compatible with their blood group.

The method of the invention also makes it possible to monitor a bone marrow grafting, by revealing very small amounts of red blood cells synthesized once again by the patient/graft.

The method of the invention also makes it possible, where appropriate, as a replacement for the Kleihauer test, to identify foetal red blood cells present in a blood sample from the mother.

In addition, the method makes it possible, for example through analyzing fluorescence signals, to quantitatively determine the proportion of antigens at the surface of the erythrocytes in the sample.

The method of the invention also makes a quantification of the antibodies possible. Thus, the result obtained may be in numerical form, and available for facilitated interpretation by means of an electronic dataprocessing system.

Moreover, the method of the invention offers the possibility of identifying a plurality of anti-erythrocyte antibodies (according to b). In general, the method makes it possible to identify any anti-ABO group specificity for the Simonin reverse test, or any other specificities in the context of screening for atypical antibodies. In general, these antibodies are capable of binding stably to their antigens, i.e. not only of binding to their antigens, but of remaining attached thereto, in particular under the conditions for carrying out the method according to the invention. These antibodies can be identified by virtue of embodiment (b) of the method according to the invention.

Moreover, it is now well known that certain particular anti-erythrocyte antibodies, by virtue of their isotype and their variable reactivity as a function of temperature, are not capable of remaining attached to their corresponding antigens. On the other hand, these antibodies are capable of activating all the proteins constituting the complement system, and in particular serum fractions C1q, C3 and C4. The result of this activation leads to the formation of modified proteins such as the C3b, C3dg and C3d proteins, which, in the case of the latter two, remain anchored in the erythrocyte membrane, whereas the initiating antibody is eliminated from the surface of the red blood cell. This complex process is, however, directly linked to the initial and specific reaction of the primary binding of the antibody to the erythrocyte antigen. Embodiment (b) of the method according to the invention, which identifies the activated serum fractions, makes it possible to identify the initial antibody.

Advantageously, the method of the invention also makes it possible to determine the isotype of the immunoglobulins present in the serum of patients, for example of pregnant women. This is of major interest for monitoring foetel anaemia. This is because it has now been demonstrated that the seriousness of haemolytic disease of the newborn depends on the isotype of the antibodies present in the mother and directed against the antigenic determinants of the child's erythrocytes (Lambin et al, Transfusion, 2002, vol 42, pp 1537-1546). Since some isotypes are more dangerous than others, it is advantageous to be able to specify the nature of the antibodies found, thus allowing the clinician to direct his or her therapeutic procedure.

Furthermore, particularly advantageously, the method according to the invention allows complete determination of the blood group of an individual in the ABO system with both the erythrocyte antigens carried by the red blood cells and the anti-erythrocyte antibodies present in the blood of the individual being determined using a single test sample, by implementing embodiments (a) and (b) of the method of the invention simultaneously and in the same receptacle.

In addition, according to a specific embodiment of the method of the invention, the latter is carried out in order to verify the cross match. It is therefore a question of cross matching all the blood group antigens (not only ABO). In this case, (i) a sample of the patient's serum or plasma is brought into contact, simultaneously, preferably in a single test receptacle, with groups of distinguishable beads carrying the erythrocytes that must be transfused, under conditions which allow the possible antibodies present to bind to the erythrocytes, (ii) the antibodies which have not bound to said erythrocytes are eliminated, (iii) the antibodies which are bound are labelled, in particular using an anti-globulin labelled, for example, with a fluorescent label, then (iv) the mixture is analyzed, preferably by flow cytometry, so as to determine whether a group of beads has bound antibodies, binding of a group of beads signifying that the erythrocytes that must be transfused are not a perfect match for the patient.

Such an application is made possible because of the high reliability of the method of the invention.

Advantageously, the method makes it possible to obtain complete, reliable results in only a few minutes. More specifically, it is possible to give a complete result in less than one hour, or even in less than 30 minutes.

Moreover, the method of the invention has very good sensitivity, at least similar to those of the techniques currently marketed, such as gel column filtration.

The method of the invention also makes it possible to considerably reduce the volume of the test sample taken. Today, the reactions are generally carried out with a test sample of 25 µl for each test, i.e. 575 µl in the case of an AAS with 20 different red blood cells and 3 screening red blood cells. To carry out the method of the invention, 50 to 100 µl only are, for example, sufficient.

BRIEF DESCRIPTION OF THE DRAWINGS

The following figures and examples illustrate the invention without limiting the scope thereof.
Figure Legend:

FIGS. 5A and 5C illustrate phenotyping in which erythrocytes are negative for a cell surface antigen or have a single anti en that is bound by a bead carrying an antibody specific for a given antigenic molecule. FIG. 5B depicts phenotyping in which erythrocytes have a pair of antigens that are bound by a bead carrying an antibody specific for a given antigenic molecule. FIG. 5D depicts phenotyping in which erythrocytes have two or three antigens that are bound by a bead carrying an antibody specific for a given antigenic molecule.

EXAMPLES

Example 1

Phenotyping and Grouping

Figure 1:
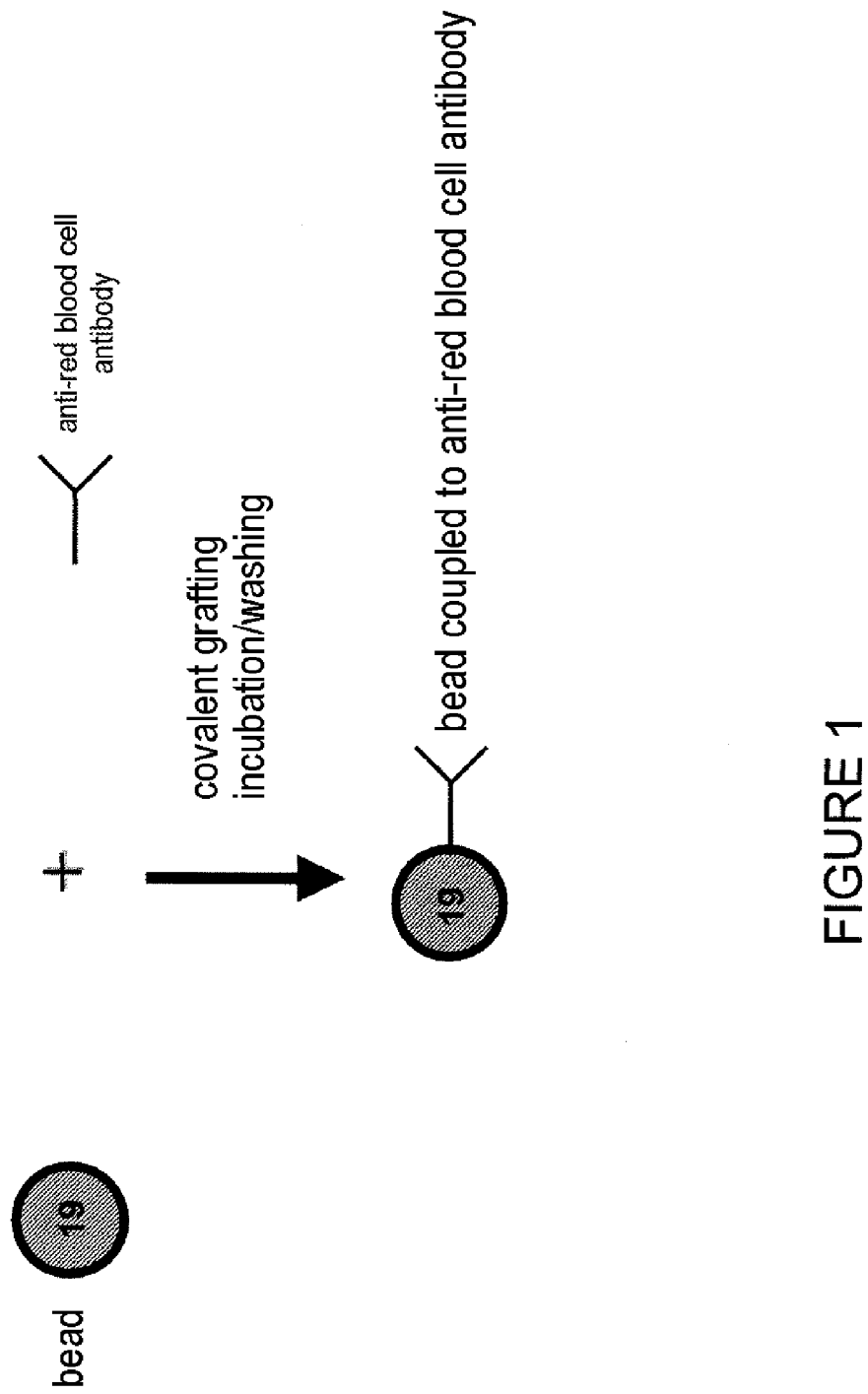
FIG. 1 is a scheme which illustrates a direct immobilization of antibodies on a Luminex® bead.

The objective of this analysis is to identify, by means of specific monoclonal antibodies, the blood group antigens present at the surface of red blood cells from donors or from patients (group ABO, RH, Duffy, Kidd, Lewis, etc.).

In order to demonstrate the possibility of phenotyping/grouping red blood cells with the technology of the invention, fluorescent beads are used to immobilize the anti-red blood cell antibodies. Antibodies of different antigenic specificities can thus be bound to various regions of beads that have different colours.

As for the red blood corpuscles, they are labelled with a fluorescent compound compatible with the wavelengths of the reporter laser of the apparatus sold under the name "Bioplex 200" by the company Bio-Rad.

After labelling, the red blood cells are incubated with the sensitized beads. It is thus possible to detect the red blood cells attached to the beads and thus to determine their antigenic specificities.

1.1—Material and Reagents

Beads:

The beads used are manufactured by Luminex (Luminex Corp., Austin Tex., United States). They are superparamagnetic beads 8 µm in diameter, composed of polystyrene and methacrylic acid (COOH function).

In this example, fluorescent superparamagnetic beads having various bead regions 19, 21, 32, 34 (Internal Standard Beads (ISB)), 71 and 98 (Blank Beads (BB)) are used. The beads (ISB) having bead region 34 are functionalized with a rhodamine derivative and are used as an internal fluorescence control. These beads should produce fluorescence values of between 5000 and 15 000 RFI.

The region-98 BB beads are saturated with bovine albumin. These beads cannot bind either antigens nor antibodies and are therefore used to verify the absence of non-specific binding. These beads should produce fluorescence values of less than 1000 RFI.

Anti-human immunoglobulin monoclonal IgG antibody, clone 125A15 (Bio-Rad).

Anti-human IgM (mu) polyclonal antibody (Bio-Rad).

Anti-D IgG (clone H2D5D2F5), anti-Fya IgG (clone 5T72A13F5A93) and anti-S IgM (clone MS94) monoclonal antibodies (Bio-Rad, Millipore).

PKH26 cell labelling kit (Sigma).

Diluting medium sold under the names "ScanLiss" code 86442 and "Stabiliss" code 86550 by the company Bio-Rad.

Gel cards sold under the name "ScanGel Coombs" code 86432 for atypical antibody screening (Bio-Rad).

Gel cards sold under the names "ScanGelRhK" code 86428 and "ScanGel Neutral" code 86430 (Bio-Rad).

Phenotyped red blood cells sold under the names "ScanPanel" code 86593 and "ScanCell" code 86595 for atypical antibody screening by the gel card technique (Bio-Rad).

Concentrated phenotyped blood cell pellets conserved in SAG-MAN medium (EFS Nord de France).

Direct Coombs-positive and/or negative red blood cells originating from patient samples.

Coating liquid or buffer (10 mM sodium phosphate, 150 mM NaCl, 0.1% (v/v) pro clin.

Bovine serum albumin (BSA) (Millipore).

PBS buffer, pH 7.4 (7 mM sodium phosphate, 2.7 mM KCl, 136 mM NaCl).

1.2—Protocol 1.2.1. Sensitization of Beads with Blood Group Antibodies

Figure 2:
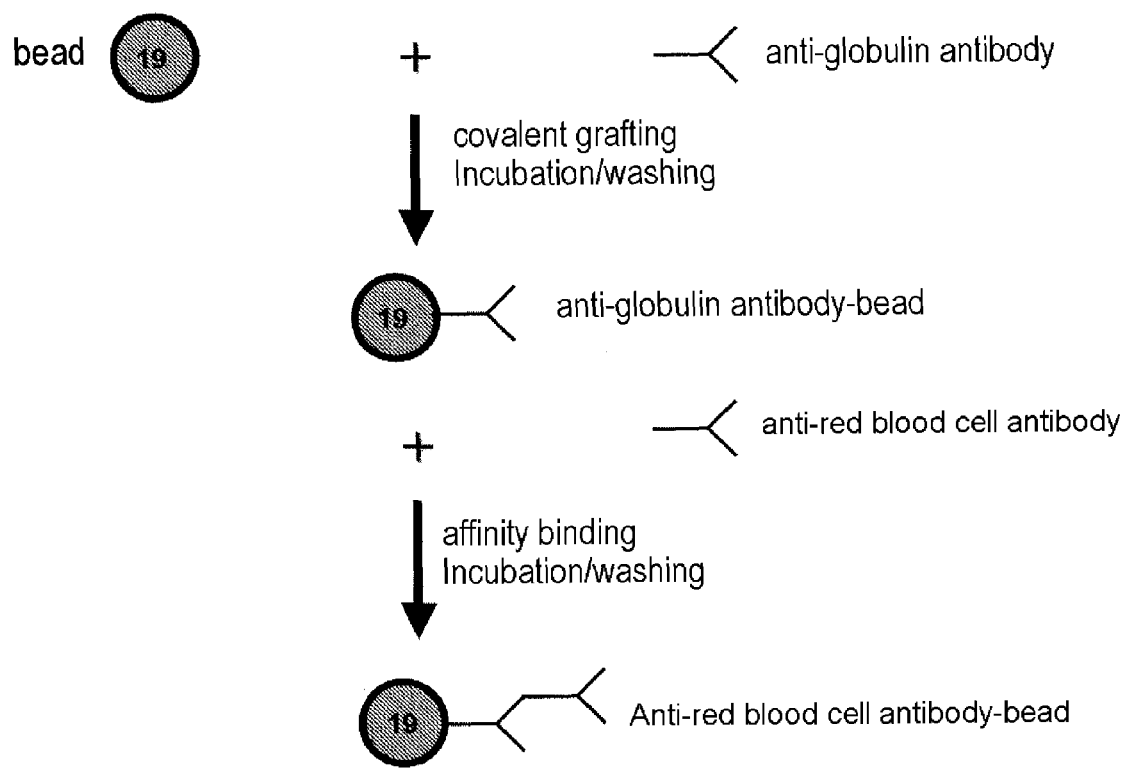
FIG. 2 is a scheme which illustrates an immobilization of antibodies on beads, by affinity, on a Luminex® bead.

The immobilization of the antibodies at the surface of the beads can be carried out according to two different principles. In the first case, the antibodies are immobilized by covalence directly on the beads (FIG. 1). The second approach consists in carrying out the immobilization of the anti-red blood cell antibodies noncovalently, by affinity. In this case, the attachment is carried out by means of an anti-immunoglobulin antibody attached by covalence to the bead in a first step (FIG. 2). This approach was selected in the examples presented.

Beads having bead regions 19, 21 and 32 were used for the covalent immobilization of the anti-human immunoglobulin. Fluorescent beads having bead region 71 were used for the covalent immobilization of the anti-human IgM. The carboxylic groups present at the surface of the beads were activated according to a technique involving a hydroxysuccinimide and a carbodiimide. The proteins could thus be immobilized via their amine groups.

The beads thus prepared are stored at +4° C. at a concentration of 3 mg/ml in PBS, pH 7.4, containing 10% (w/v) of BSA, 0.5% (v/v) of Tween 20 and 0.09% (w/v) of sodium azide.

The beads carrying the immobilized anti-human immunoglobulin can be sensitized with anti-D IgG or anti-Fya IgG blood group antibodies. The anti-immunoglobulin in fact allows the IgGs to bind via their Fc fragment. The blood group antibodies are therefore non-covalently immobilized on the beads using this principle. Each bead region is sensitized with an antibody of different specificity. The anti-immunoglobulin chosen has a high affinity for human immunoglobulins, thus allowing this binding to be stable over time.

The nonpurified anti-D and anti-Fya are used at the respective final concentrations of 30 and 10 µg/ml with beads functionalized with anti-Fc at 80 µg/mg.

The sensitization with the blood group antibodies is carried out in PBS, pH 7.4, with agitation at 37° C. for one hour.

After sensitization, the beads are rinsed several times and then stored at +4° C. in PBS, pH 7.4.

The beads carrying the immobilized anti-mu can be sensitized with the anti-S IgM. The anti-mu in fact allows binding of IgMs. The affinity of this anti-mu polyclonal serum is sufficient to ensure binding that is stable over time. The nonpurified anti-S is immobilized on beads functionalized with anti-mu at 40 µg/mg. The sensitization is carried out in PBS, pH 7.4, with agitation at 37° C. for one hour. After sensitization, the beads are rinsed several times and then stored at +4° C. in PBS, pH 7.4. Before incubation with the red blood cells (test per se), the beads sensitized with the blood group antibodies are mixed with control region-34 beads (ISB) and control region-98 beads (BB).

1.2.2. Labelling of Red Blood Cells

Figure 3:
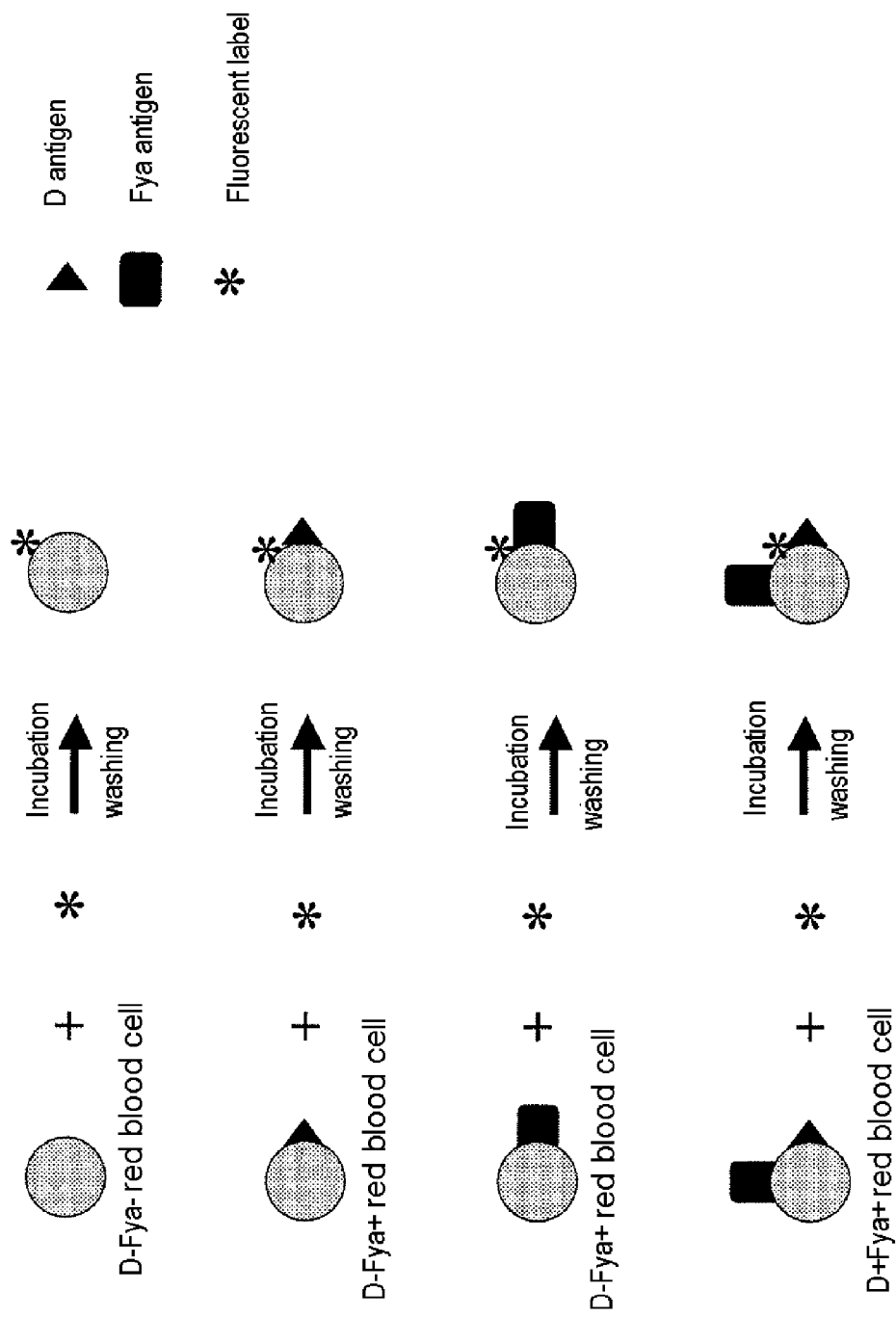
FIG. 3 is a scheme which illustrates the labelling of red blood cells of various phenotypes with a fluorescent intramembrane compound.

The labelling of red blood cells with a fluorescent compound can be carried out using various principles. In the examples presented, the red blood cells are labelled using PKH26, which is a fluorophore that is inserted into the red blood cell membrane. Red blood cells of varied phenotypes can thus be labelled according to an identical protocol (FIG. 3).

PKH26 is a fluorescent probe sold by the company Sigma. This probe has a maximum excitation at 551 nm and a maximum emission at 567 nm.

The kit includes the fluorescent label, which has a long aliphatic chain allowing it to be incorporated into the lipid layer of cell membranes, and also an isoosmotic aqueous diluent containing no salt, buffer or organic solvent. This diluent makes it possible to maintain the cell viability, the label solubility and the labelling efficiency at high levels.

The labelling of red blood cells with PKH26 is carried out using the protocol recommended by the manufacturer. The red blood cells thus labelled are diluted in the Stabiliss buffer and stored in the dark at +4° C.

The quality, the viability and the stability of the labelled red blood cells are verified over time by carrying out phenotyping assays according to a gel technique. The antigenic integrity of the labelled red blood cells is compared with that of nonlabelled red blood cells. The quality and the stability of the fluorescent labelling are, for their part, studied by carrying out fluorescence measurements using the "Bioplex 200" apparatus from Bio-Rad.

1.2.3. Incubation of Blood Group Antibody-Beads and Red Blood Cells

In order to demonstrate the feasibility and verify the specificity of the grouping according to the technology in accordance with the invention, the inventors carried out the reactions in a unitary manner. In this case, the beads functionalized with the blood group antibodies are incubated individually with red blood cells of varied phenotypes.

In the case of the multiplexed reactions, different blood samples are brought into contact individually with beads having different bead regions and sensitized with antibodies of different specificities. This type of experiment made it possible to verify the possibility of detecting several antigenic blood group specificities in the same test sample.

The sensitized beads are mixed with the red blood cells so as to obtain a red blood cell/bead ratio of approximately 50 to 150. The mixture is incubated for 15 minutes with agitation at 37° C.

After incubation, the bead-red blood cell complexes are washed several times with distilled water.

1.2.4. Measurements by Flow Cytometry Using the "Bioplex 200" Automated Device from the Company Bio-Rad After the final wash and before the measurements, the complexes are diluted with 185 µl of "coating liquid" medium. For each test, 25 µl of suspension are automatically injected into the apparatus. The measurements are carried out by capture of 250 beads per region. For each grouping/phenotyping series, systematic controls are carried out in order to verify the specificity of the reactions studied.

1.3. Simplex/Multiplex Phenotyping/Grouping Examples

The objective of this series of tests is to demonstrate the feasibility of the phenotyping/grouping of red blood cells in unitary and/or multiplexed mode. The D, Fya and S antigens are selected as models. Beads sensitized with an anti-human immunoglobulin or anti-mu chain antibody are used to immobilize anti-D, anti-Fya and anti-S antibodies.

1.3.1. Unitary phenotyping of RH D-positive red blood cells

The beads sensitized with the anti-D antibody were incubated with Rh D-positive and Rh D-negative red blood cells labelled with PKH26, using a red blood cell number/bead number ratio of 150.

Two RH D-positive red blood cells and two RH D-negative red blood cells were used.

Each sample was injected into the apparatus in duplicate.

The RH D-positive red blood cells produce strongly positive signals of the order of 21 000 to 25 000 RFI, whereas the RH D-negative red blood cells exhibit negative signals of between 40 and 400 RFI.

The ISB 34 control beads that give signals of the order of 6500 RFI and the BB 98 control beads that give less than 1000 RFI validate the results. The various negative controls carried out exhibit signals of between 15 and 400 RFI, confirming the specificity of the reactions. The RH D-positive and RH D-negative red blood cells do not in fact bind to the beads in the absence of anti-D antibodies.

These results demonstrate the possibility of distinguishing very clearly the RH D-positive and RH D-negative red blood cells and therefore of identifying the D antigen at the surface of red blood cells.

The unitary phenotyping of Fya and S red blood cells can be carried out according to the same principle, using isotype G-specific or isotype M-specific antibodies.

1.3.2. Multiplex Phenotyping of D, Fya and S Red Blood Cells

The principle of the multiplexed phenotyping is summarized in FIGS. 5A to 5D. In this case, region-19 beads sensitized with an anti-D antibody were mixed with region-21 beads sensitized with an anti-Fya antibody and also with region-71 beads sensitized with an anti-S antibody.

This mixture of beads was incubated with red blood cells having different D, Fya and S phenotypes: D+Fya+S+/D+Fya–S–/D–Fya+S–/D–Fya–S–/D–Fya–S+/D–Fya+S+/D+Fya–S+/D+Fya+S–. A red blood cell number/bead number ratio of 50 was used. Positive signals of between 13 000 and 29 000 RFI are obtained when the beads sensitized with a given antibody bind a red blood cell having the corresponding antigenic specificity.

A perfect correlation is observed between the fluorescent signals measured and the phenotype of the red blood cells used to carry out the test.

When a bead sensitized with an antibody is brought into contact with a red blood cell that does not carry the corresponding antigen, a signal of less than 1000 RFI is obtained. Moreover, the controls carried out with beads not antibody-sensitized produce negative signals irrespective of the red blood cell used.

These results demonstrate that the signals measured are specific: the bead-red blood cell binding occurs only when an antigen-antibody pair is involved.

The results obtained with the control beads ISB 34 (11 000 RFI) and BB 98 (less than 1000 RFI) validate the analyses.

The intra-test variation coefficients are between 1% and 10%, which demonstrates a satisfactory intra-test reproducibility.

These results demonstrate the feasibility of the three-parameter multiplexed phenotyping of red blood cells according to the technology according to the invention.

1.3.3. Multiplexed Phenotyping of Direct Coombs-Positive (CD+) Red Blood Cells

Figure 6:
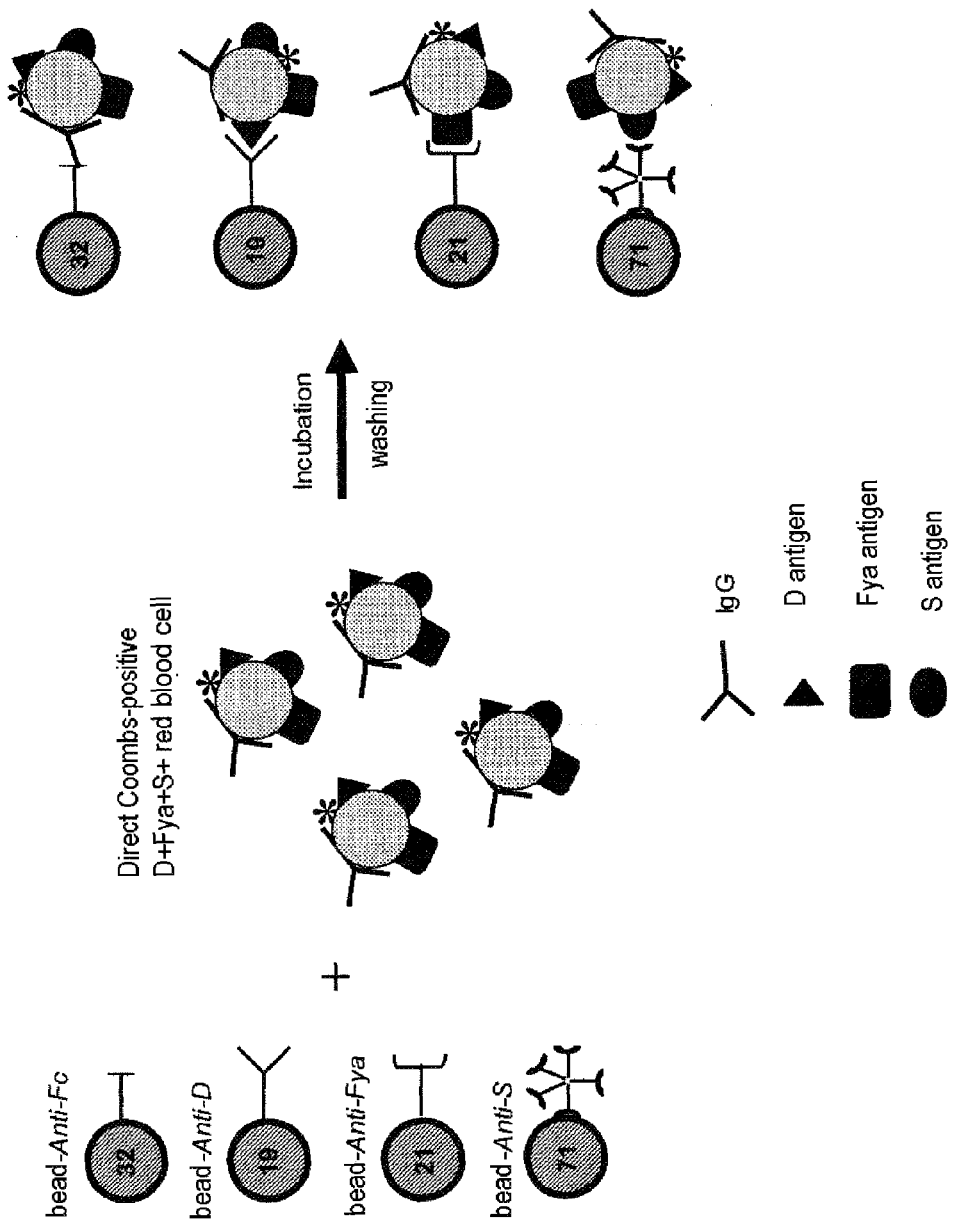
FIG. 6 is a scheme which illustrates the simultaneous identification and multiplexed phenotyping of red blood cells from a "direct Coombs-positive" patient.

The use of the multiplexed approach with microbeads makes it possible to identify the CD+ nature and to phenotype the red blood cells simultaneously according to a principle described in FIG. 6.

Region-32 beads sensitized with the anti-Fc antibody are mixed with region-19, -21 and -71 beads respectively sensitized with an anti-D, anti-Fya and anti-S antibody. The CD+ red blood cells, sensitized in vivo with an antibody, can bind to the anti-human immunoglobulin carried by the region-32 beads, thereby making it possible to identify the CD+ characteristic. Moreover, these red blood cells can also bind to the region-19, -21 and -71 beads carrying the antibodies specific for the D, Fya and S antigens, according to the specificities present on the red blood cell membrane.

This approach was demonstrated using a red blood cell number/bead number ratio of the order of 40.

The ISB 34 and BB 98 control beads produce expected signals, i.e. respectively of the order of 13 000 RFI and less than 1000 RFI, and validate the results.

The two CD+ red blood cells produce positive signals greater than 30 000 RFI with the region-32 beads sensitized with the anti-human immunoglobulin antibody. The two CD– negative red blood cells produce, for their part, negative signals of less than 500 RFI with this same bead region. These results demonstrate the possibility of identifying CD+ red blood cells by virtue of their specific binding using an antiglobulin coupled beforehand to a bead of given bead region.

Furthermore, the results also demonstrate that the multiplexed phenotyping of the erythrocyte antigens of CD+ red blood cells can be carried out simultaneously with the identification of the CD+ nature. In fact, one of the CD+ red blood cells is phenotyped D+Fya–S– and the other D+Fya+S+.

The S phenotype of these two samples was verified according to a conventional technique using anti-S antibodies of IgM type. The results obtained are perfectly correlated with those obtained according to the new technique.

On the other hand, as regards the anti-Fya phenotype, this same analysis could not be carried out. There is in fact no reagent of IgM type for phenotyping red blood cells.

However, a difference is observed for the Fya phenotype according to the CD+ red blood cell analyzed, which validates the results and makes it possible to exclude a phenomenon of nonspecific binding.

The variation coefficients are for most of the samples between 1% and 5%, which shows a satisfactory intra-test reproducibility.

Example 2

Atypical Antibody Screen Unitary and Multiplexed Methodology

The atypical antibody screen (AAS) is generally carried out according to the most sensitive methods (filtration through a gel sold by the company Bio-Rad in the "ScanGel" range, sold by the company Diamed under the name "Diamed ID", or according to an immunoadhesion methodology in microplate format, sold by the company Immucor, Capture® range). In the first two cases, it uses red blood cells the phenotype of which is known and which are incubated with the serum or plasma sample to be examined. The specific antibodies, possibly present, bind to the surface of the red blood cells. They are subsequently revealed using a reagent containing an anti-human immunoglobulin antibody. In the case of a positive reaction, a red blood cell agglutinate is formed. If the reaction is negative, the red blood cells are free and no aggregate is formed. By using panels of red blood cells which have or do not have various antigens, it is then possible to determine the specificity of the antibodies present in the sample.

The objective of this series of tests is to use beads on which phenotyped red blood cells are immobilized via poly-L-lysine (PLL) in order to carry out the detection of IgG-type blood group antibodies according to the technology in accordance with the invention using a flow cytometer.

A phycoerythrin (PE)-labelled anti-Fc antibody conjugate is used to detect the atypical antibodies bound.

2.1—Material and Reagents

Fluorescent superparamagnetic beads having bead regions 17, 21, 32 and 36

The beads are stored at +4° C. in PBS buffer, pH 7.4.

Region-34 (internal standard beads (ISB)) and region-98 (blank beads (BB)) control fluorescent beads.

Poly-L-lysine (PLL) of molecular weight 70 000-130 000.

Anti-human immunoglobulin monoclonal IgG antibody, clone 125A15 (Bio-Rad) coupled to phycoerythrin (PE) with a ratio of 2 antibody equivalents per PE equivalent.

Anti-D (clone H2D5D2F5) and anti-Fya (clone 5T72A13F5A93) monoclonal IgG antibodies (Bio-Rad).

Anti-RH1 National Standard (Centre de Reference pour les Groupes Sanguins [Blood Group Reference Centre], France).

Phenotyped red blood cells sold under the names "Scan-Cell" and "ScanPanel" for atypical antibody screening (Bio-Rad).

Coating liquid or buffer (10 mM sodium phosphate, 150 mM NaCl, 0.1% (v/v) proclin).

Bovine serum albumin (BSA) (Millipore).

PBS buffer, pH 7.4 (7 mM sodium phosphate, 2.7 mM KCl, 136 mM NaCl).

2.2—Protocol 2.2.1. Sensitization of Beads with PLL

The region-17, -21, -32 and -36 neutral beads are incubated with 25 µg/ml of PLL in PBS, pH 7.4, for 18 hours at ambient temperature and with agitation. At the end of this step, the beads are washed in PBS, pH 7.4, and then used to immobilize the red blood cells.

2.2.2. Immobilization of Red Blood Cells on the Beads

The bead-red blood cell reagents are prepared by mixing the PLL-coated beads and the red blood cells in a red blood cell number/bead number ratio equal to 100. The incubation is carried out in PBS, pH 7.4, with agitation for 5 minutes at ambient temperature. Each bead region is used to immobilize a single type of red blood cell of known and different phenotype. At the end of this step, the bead-PLL-red blood cell reagents are washed with PBS, pH 7.4, and then with distilled water. The bead-red blood cell reagents thus prepared are stored in PBS, pH 7.4, at +4° C.

Figure 4:
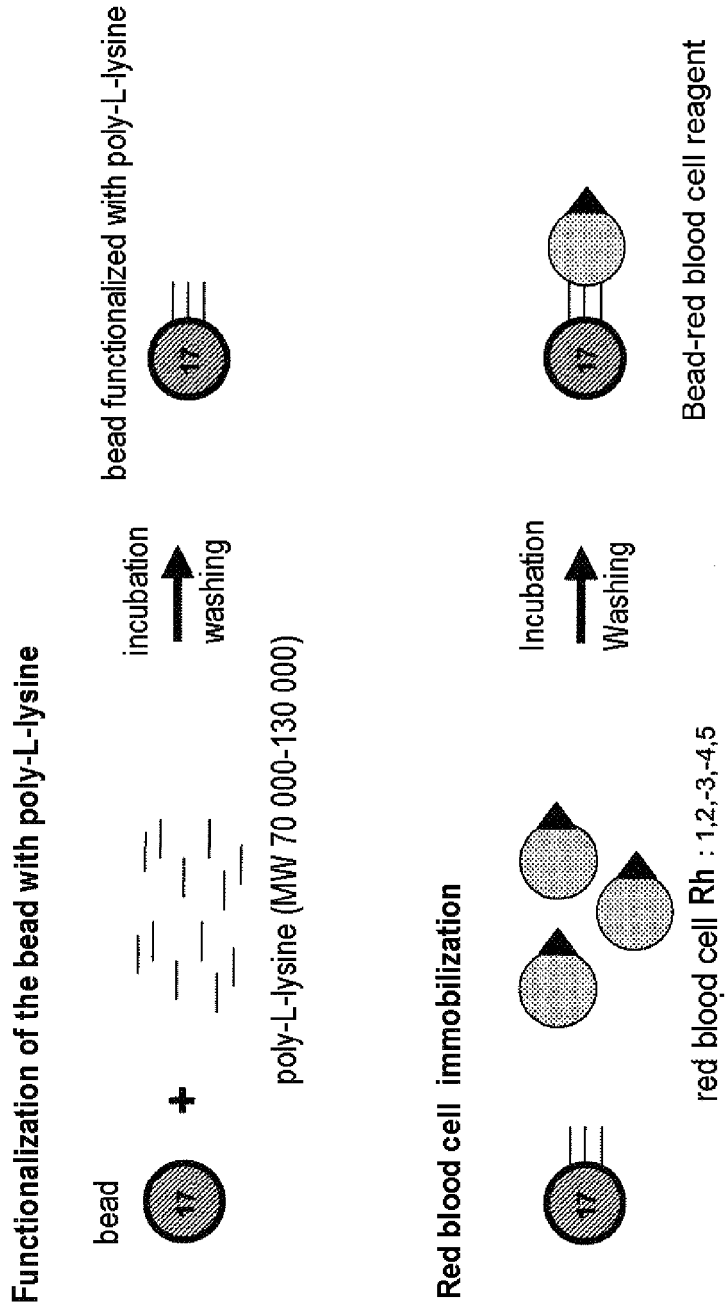
FIG. 4 is a scheme which illustrates a procedure for immobilizing red blood cells on Luminex® beads by means of poly-L-lysine.
Figure 5A:
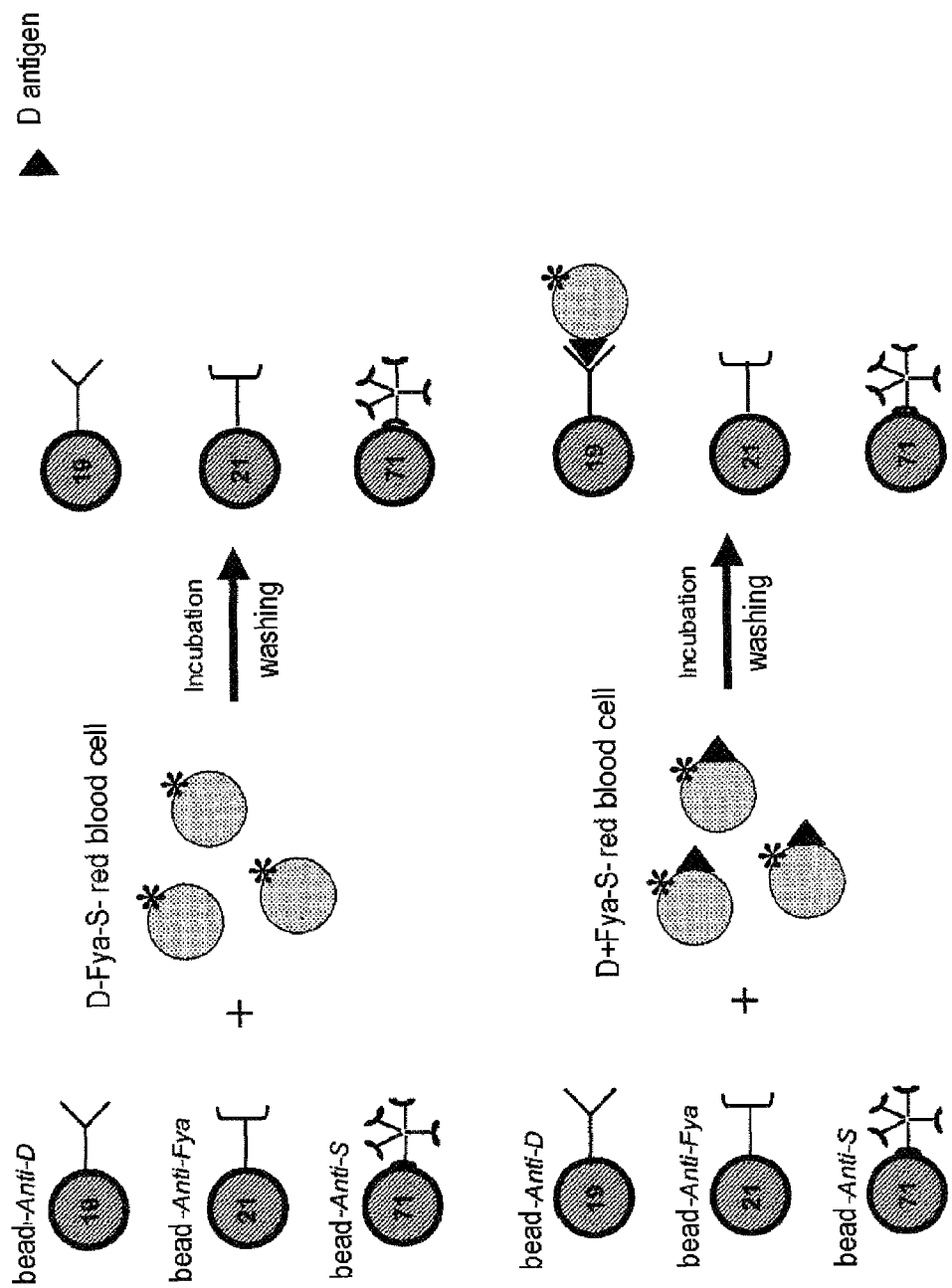
FIGS. 5A to 5D show various embodiments of multiplexed phenotyping of red blood cells.
Figure 5B:
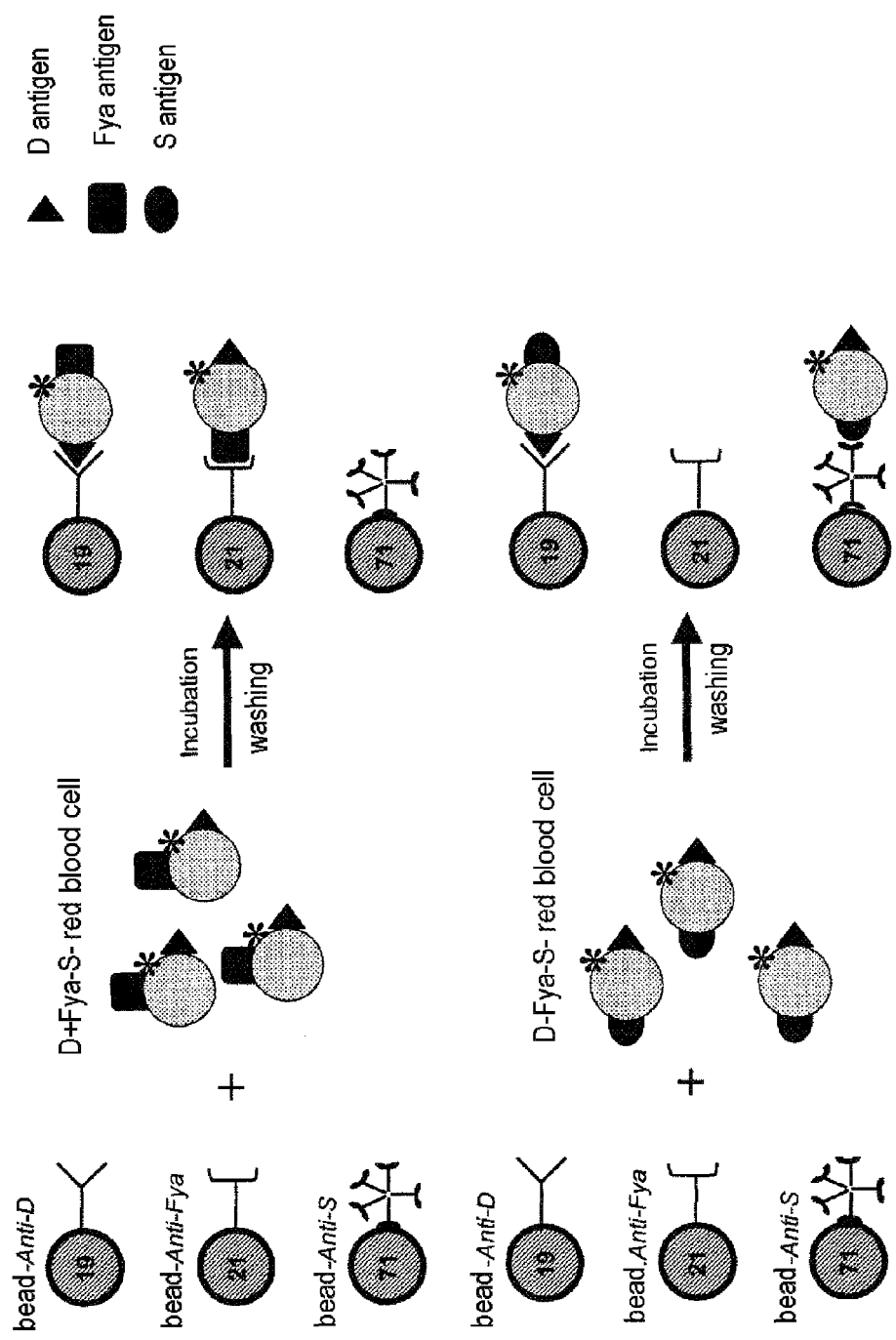
Figure 5C:
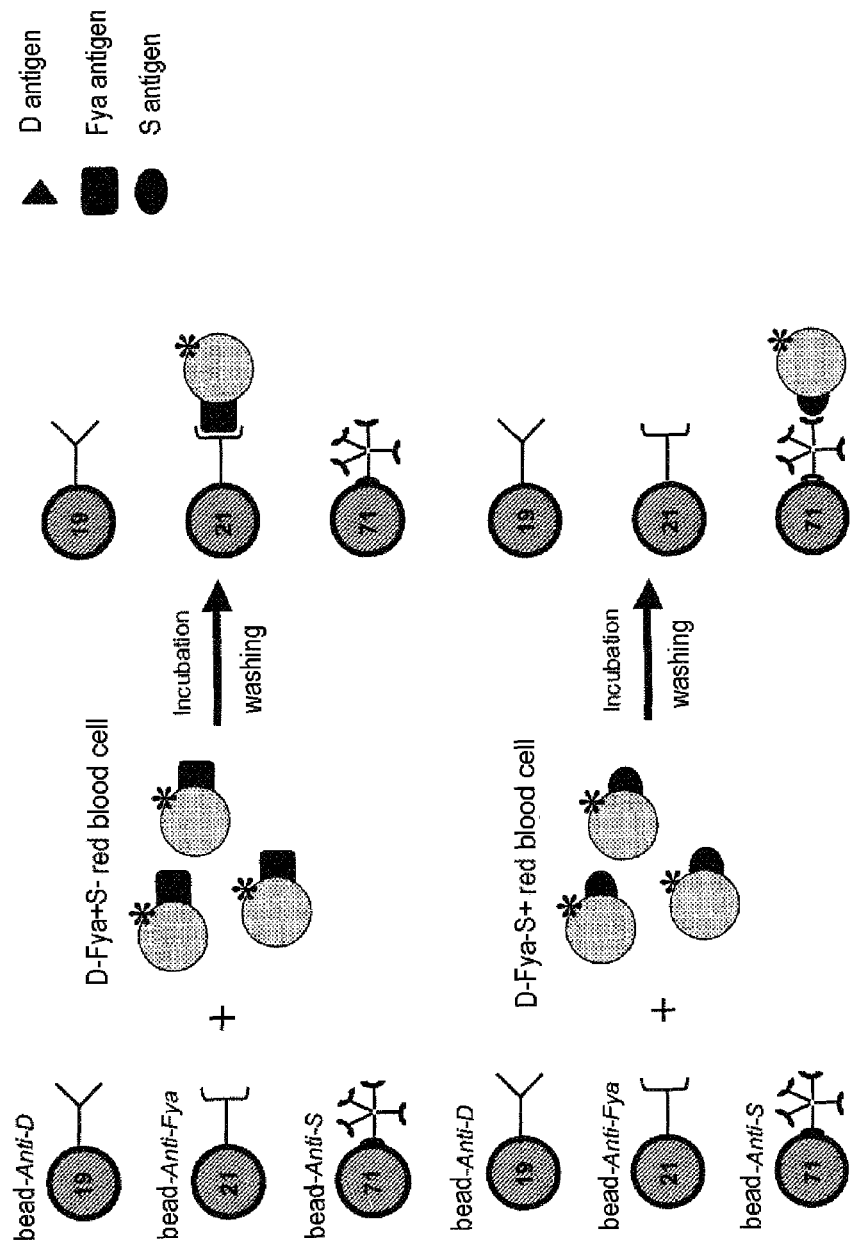
Figure 5D:
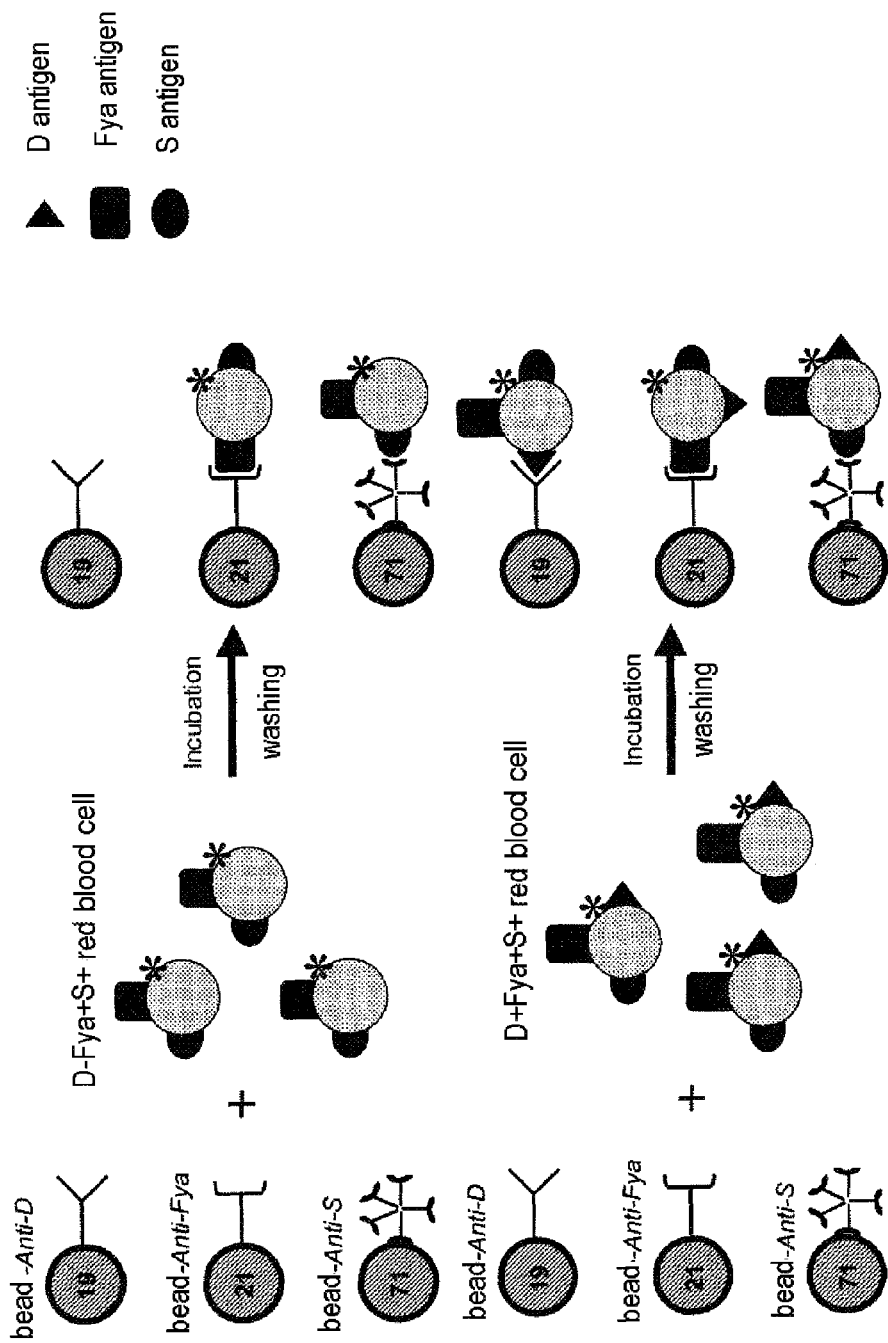

The principle of immobilizing red blood cells on beads by means of PLL is summarized in FIG. 4.

The binding of the red blood cells by means of PLL is sufficiently solid so as not to allow them to detach during the tests and analyses.

Before incubation with the antibodies being screened, the bead-PLL-red blood cell reagents are mixed with the region-34 (ISB) and region-98 (BB) control beads.

2.2.3. Reaction of the Bead-PLL-Red Blood Cell Reagents with the Antibodies

In the case of unitary reactions, the bead-red blood cell reagents are used individually and incubated with different antibodies in order to verify the specificity of the reactions. In order to carry out the multiplexed reactions, the beads sensitized with various red blood cells of known phenotypes are mixed and then incubated with the antibody or antibodies to be detected.

The antibodies to be measured are diluted either in protein-rich buffer (0.15 M NaCl, 60 g/l BSA) or in PBS buffer, pH 7.4, before incubation with the bead-PLL-red blood cell reagents.

In all cases, 125 µl of bead-PLL-red blood cell reagents are mixed with 125 µl of antibodies and then incubated for 60 minutes with agitation at 37° C.

After incubation, the complexes are washed several times.

2.2.4. Revelation of the Complexes Using PE-Labelled Anti-Fc

In order to detect the bead-PLL-red blood cell-antibody complexes, an antibody specific for the Fc fragment of human immunoglobulins, labelled with PE, is used. This antibody conjugate is used at a concentration of 60 µg/ml in PBS pH 7.4, and is incubated with the complexes for 15 minutes at 37° C. with agitation. The complexes are then washed with distilled water.

2.2.5. Measurements

After the final wash and before the measurements, the complexes are taken up with 185 µl of coating liquid. For each test, 25 µl of suspension are injected into the apparatus. The measurements are carried out by capture of 250 beads per region.

For each series, systematic controls are carried out in order to verify the specificity of the reactions studied. For each antibody tested, a negative control is carried out using phenotyped red blood cells not carrying the corresponding antigenic specificity.

2.3—Simplex/Multiplex AAs Examples 2.3.1. Multiplexed Detection of the Anti-D Monoclonal Antibody in a Protein-Rich Medium The antibody was detected using a mixture of beads of various bead regions, sensitized with red blood cells of known phenotypes.

Region-17 beads coated with PLL were used to immobilize a red blood cell phenotyped D, CC, ee. A red blood cell of phenotype D, cc, EE was immobilized on region-32 beads and a red blood cell of phenotype d, cc, ee was immobilized on region-36 beads.

The region-36 beads coated with D-negative red blood cells were used as negative controls in order to verify the specificity of the reaction.

The sensitized beads were mixed and then incubated with the anti-D monoclonal antibody prepared at various concentrations in 0.15M NaCl buffer, 60 g/l BSA. The detection was carried out with the PE-labelled anti-Fc conjugate.

Figure 7:
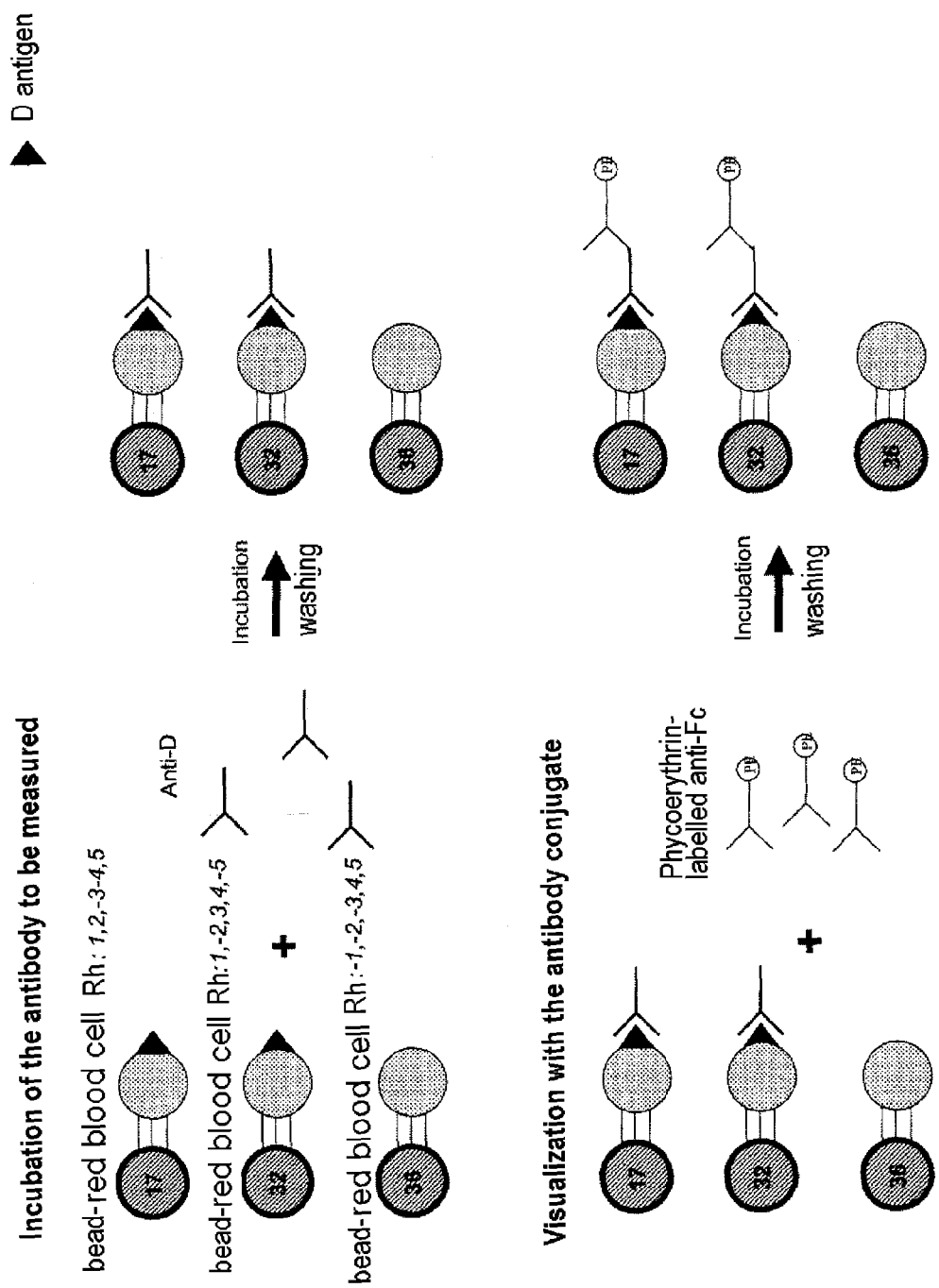
FIG. 7 is a scheme which illustrates the multiplex detection of the anti-D antibody.

The principle of this approach is summarized in FIG. 7.

Figure 8:
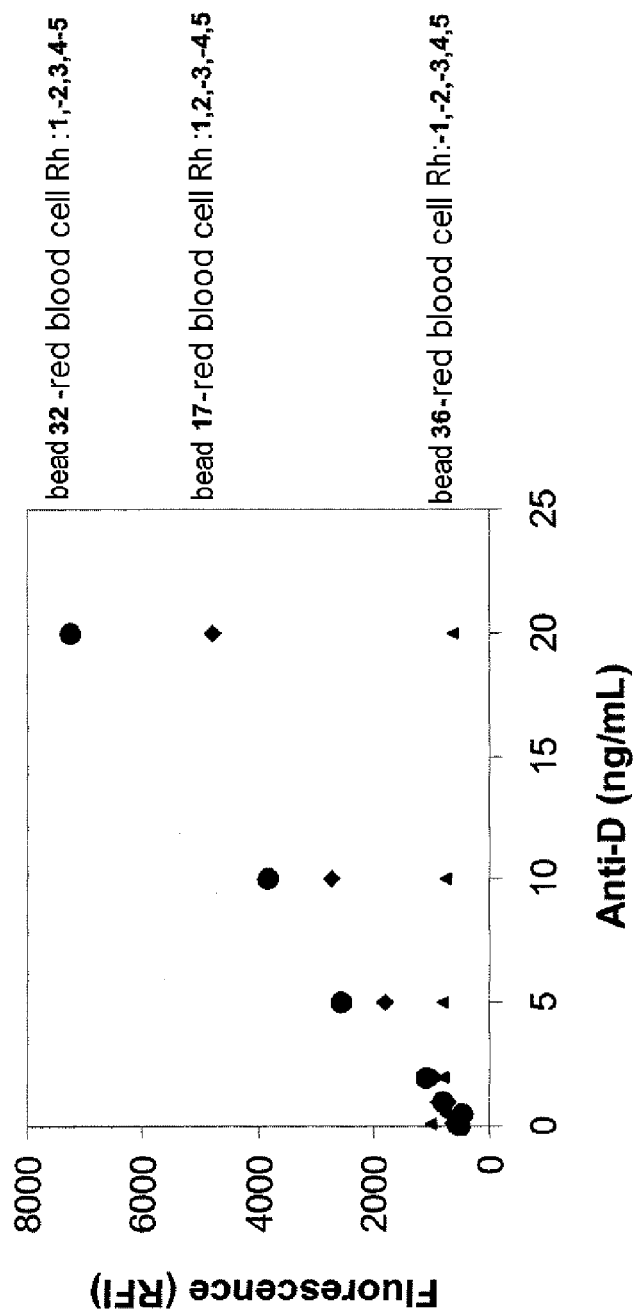
FIG. 8 is a graph which shows the multiplex calibration of the anti-D antibody.

The results are given in FIG. 8.

It is observed that the response with respect to the red blood cells that do not have the D antigen (bead 36) exhibits values of less than or equal to 1000 RFI which correspond to negative responses. On the other hand, with the beads supporting red blood cells having the D antigens (beads 32 and 17), the values obtained are much higher (of the order of 2000 to more than 7000 RFI). Furthermore, the positive signals are correlated with the concentration of anti-D antibody involved, the detection limit according to this format being around 5 ng/ml.

For the same concentration of anti-D antibody, variations in positivity can be noted according to the phenotype of the red blood cell attached to the surface of the beads. This phenomenon is known in immunohaemotology and is related to the difference in antigenic expression of the D antigen.

These results demonstrate the specificity of the detection carried out with the multiplex format under consideration.

Moreover, the region-34 and -98 control beads give the expected signal levels, i.e., respectively, of the order of 11 000 RFI and less than 1000 RFI.

2.3.2. Unitary Detection of the Reference Anti-D Polyclonal Antibody in a Reference Serum A CNRGS [National Blood Group Reference Centre] anti-D national reference standard was used to carry out the unitary detection of the anti-D antibody in a protein-rich medium approaching a plasma.

A red blood cell of phenotype D, cc, EE was immobilized on region-32 beads. A negative control was carried out separately using a red blood cell of phenotype d, cc, ee immobilized on region-21 beads. The standard was diluted in a 0.15M NaCl buffer containing 60 g/l of BSA.

Figure 9:
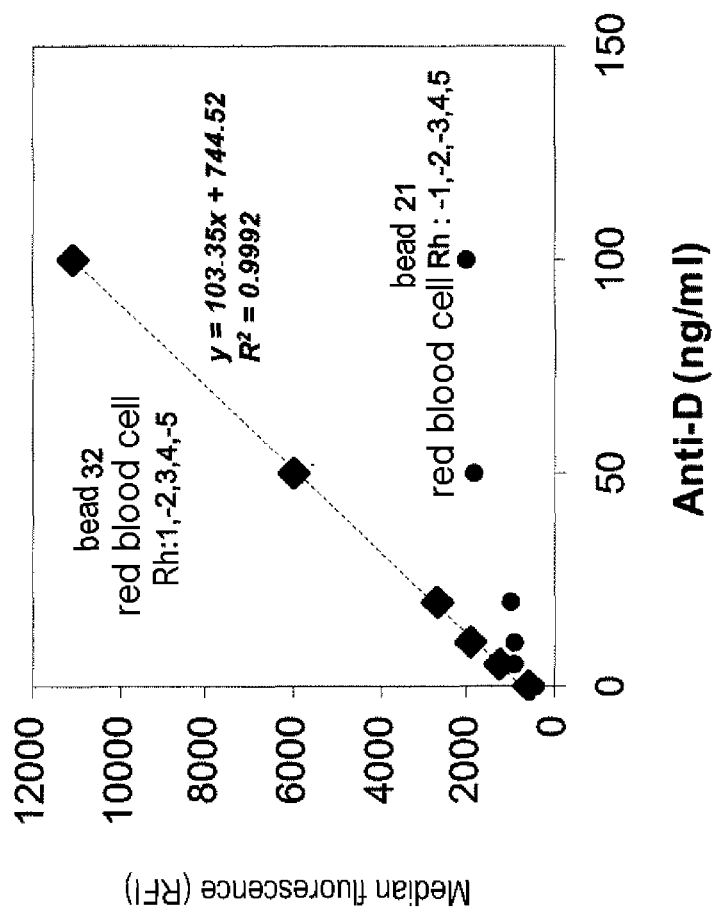
FIG. 9 is a graph which shows the simplex calibration of the anti-D antibody in the reference serum from the Centre de Reference pour les Groupes Sanguins (CNRGS) [Blood Group Reference Centre].

The results, given in FIG. 9, show that the reference antibody can be detected at a concentration of less than 1 ng/ml in the presence of red blood cells of RH D phenotype. The dynamic range extends linearly to at least 100 ng/ml, the results obtained in the presence of beads carrying an RH D-negative red blood cell being less than 650 RFI. The values for the control beads (ISB and BB) make it possible to validate the results observed.

2.3.3. Multiplexed Detection of Several Monoclonal Blood Group Antibodies

In this case, the region-17 beads were sensitized with red blood cells of phenotype D, CC, ee, Fya–b+, the region-32 beads were sensitized with red blood cells of phenotype dd, cc, ee, Fya+b– and the region-21 beads were sensitized with red blood cells of phenotype D, cc, EE, Fya–b+.

Figure 10:
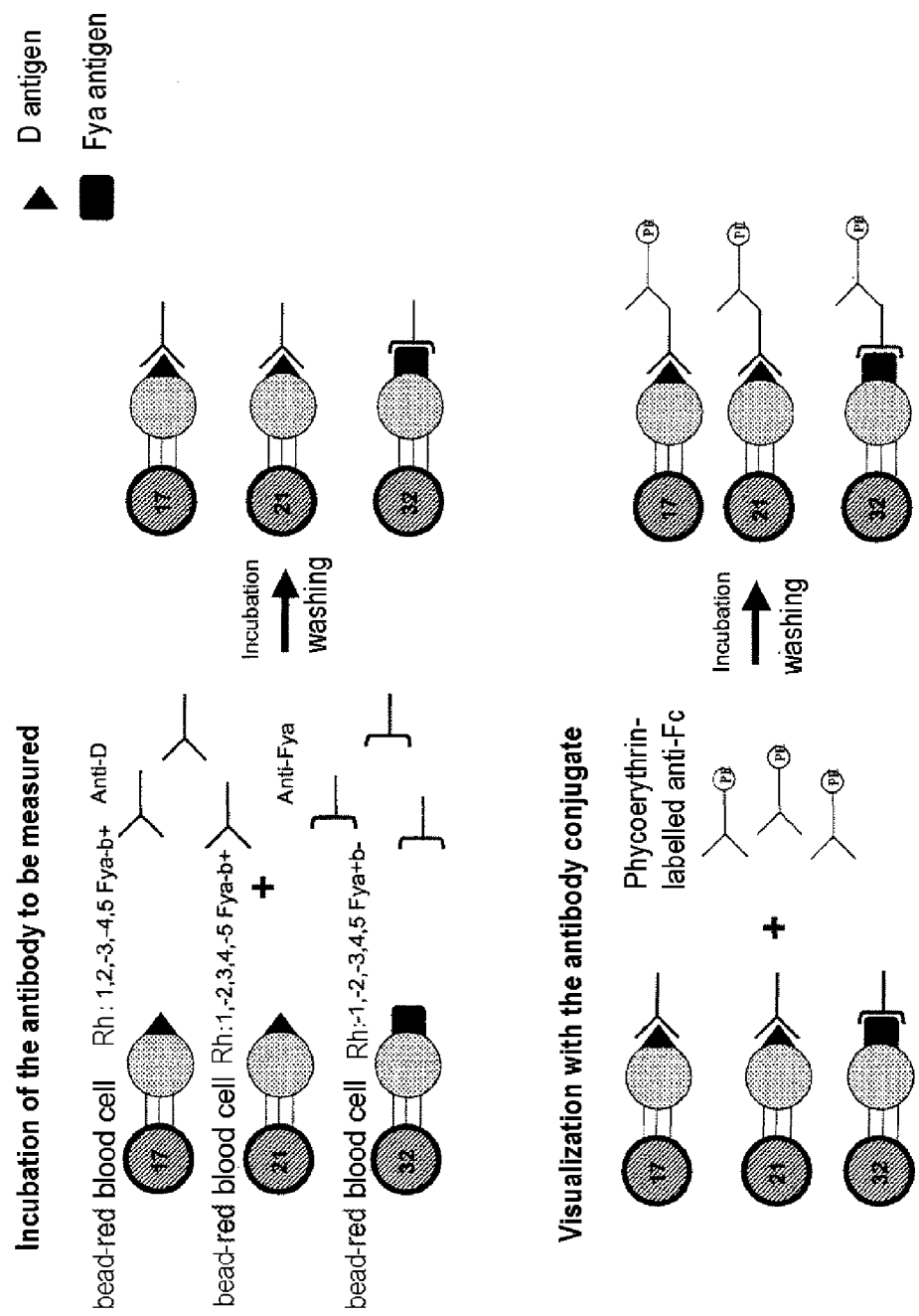
FIG. 10 is a scheme which illustrates the multiplex detection of anti-D and anti-Fya antibodies.

The 3 types of beads were mixed and then incubated with the anti-D and anti-Fya monoclonal antibodies used separately or as a mixture. All the steps were carried out in PBS, pH 7.4. The principle of this approach is given in FIG. 10.

The region-34 and -98 internal control beads produce the expected signal levels, i.e., respectively, of the order of 11 000 RFI and less than 1000 RFI. A perfect correlation is observed between the phenotype of the red blood cells used during the sensitization of the beads and the antibodies present in the reaction mixtures. Thus, positive signals of the order of 6000 to 25 000 RFI are observed when the anti-D and anti-Fya antibodies are incubated in the presence of red blood cells carrying the corresponding antigens. The incubation of the antibodies with red blood cells not carrying the corresponding antigens produces negative signals of less than 1000 RFI. The reactions are specific.

These results demonstrate the validity of the approach considered for carrying out the multiplexed detection of several antibodies present in the same sample.

Example 3

Cross Match

The objective of this analysis is to be sure that, in the context of a transfusion of one or more blood cell concentrates from donors to a recipient, there is complete donor-recipient compatibility and, where appropriate, to demonstrate an incompatibility linked to the presence of antibodies in the recipient's plasma, directed against blood group structures carried by the red blood cells of the donor(s).

In order to demonstrate the possibility of carrying out the cross match in the technology of the invention, fluorescent beads are used to immobilize the donor's red blood cells via poly-L-lysine (PLL). This immobilization is carried out by simple contact between the beads and the donor's red blood cells, for a minimum amount of time (5 min) and extemporaneously.

These beads are then placed in the presence of the recipient's plasma or serum. The possible presence of antibodies from the recipient directed against the donor's antigens is detected by an anti-Fc antibody conjugate labelled with phycoerythrin (PE).

3.1. Material and Reagents

Fluorescent superparamagnetic beads having bead region 38

The beads are stored at +4° C. in PBS buffer, pH 7.4.

Region-34 (internal standard beads (ISB)) and region-98 (blank beads (BB)) control fluorescent beads.

Poly-L-lysine (PLL) of molecular weight 70 000-130 000.

Anti-human IgG mouse IgG monoclonal antibody, clone 125A15 (Bio-Rad) coupled to phycoerythrin (PE) with a ratio of 2 antibody equivalents per PE equivalent.

Phenotyped blood cell concentrates conserved in SAG-MAN medium (EFS Nord de France).

Diluting medium sold under the name "ScanLiss" code 86442 by the company Bio-Rad Coating liquid or buffer (10 mM sodium phosphate, 150 mM NaCl, 0.1% (v/v) proclin).

Bovine serum albumin (BSA) (Millipore).

PBS buffer, pH 7.4 (7 mM sodium phosphate, 2.7 mM KCl, 136 mM NaCl).

3.2. Protocol

3.2.1. Sensitization of Beads with PLL

The bead-PLL reagent is prepared by incubating region-38 neutral beads with 50 µg/ml of PLL in PBS, pH 7.4, for 18 hours at ambient temperature and with agitation. At the end of this step, the bead-PLL reagent is washed with PBS buffer, pH 7.4, and then used to immobilize the donor red blood cells.

3.2.2. Extemporaneous Immobilization of Donor Red Blood Cells on the Beads

The bead-PLL reagent is brought into contact with the red blood cells of the various donors, each donor being treated separately.

Twenty-five microlitres of bead-PLL reagent are mixed with 25 µl of donor red blood cells diluted in ScanLiss in a red blood cell number to bead number ratio equal to 100.

The incubation is carried out with agitation for 5 minutes at ambient temperature.

After incubation, the bead-PLL-red blood cell complexes are washed several times with distilled water and then taken up in 25 µl of PBS-BSA 10 g/l, pH 7.4.

The principle of immobilization of red blood cells on the beads by means of PLL is summarized in FIG. 4.

The attachment of the red blood cells by means of the PLL is sufficiently solid to prevent them from detaching during the test and the analyses.

The bead-PLL-red blood cell complexes thus prepared and the region-34 and region-98 control beads are then incubated with the samples to be tested.

3.2.3. Reaction of the Bead-PLL-Red Blood Cell Complexes with the Antibodies Twenty-five microlitres of bead-PLL-red blood cell complex are mixed with 50 µl of patient plasma or serum to be tested and incubated for 15 minutes with agitation at 37° C. After incubation, the complexes are washed several times with PBS buffer, pH 7.4.

3.2.4. Visualization of the Complexes with the PE-Labelled Anti-Fc

To detect the bead-PLL-red blood cell-antibody complexes, a PE-labelled antibody specific for the human immunoglobulin Fc fragment is used. This antibody conjugate is used at a concentration of 5 µg/ml in PBS, pH 7.4, and is incubated with the complexes for 15 minutes at 37° C. with agitation. The complexes are then washed several times with PBS buffer, pH 7.4.

3.2.5. Flow Cytometry Measurements Using the "Bioplex 200" Apparatus from the Company Bio-Rad After the final wash and before the measurements, the complexes are taken up with 35 µl of the coating liquid. For each test, 25 µl of suspension are injected into the apparatus. The measurements are carried out by capture of 250 beads per region.

Various donor red blood cells were used. For each donor red blood cell, negative controls were tested in order to verify the specificity of the reactions studied.

3.3. Cross Match Example

Region-38 beads coated with PLL were used to immobilize red blood cells from three different donors: one donor of phenotype D, cc, kk, SS, one donor of phenotype dd, CC, kk and one donor of phenotype dd, cc, K+, ss. Each donor-recipient pair was tested separately.

The sensitized beads were incubated with various sera known to exhibit anti-D, anti-c, anti-K or anti-S reactions. These sera represent sera from recipients that may potentially show an incompatible cross match with the chosen donor red blood cells. These sera were chosen so as to react with blood antigen systems that are different in terms of structure and antigen presentation and also in terms of antigen density on the red blood cell.

Twelve donor plasmas were also tested and used as negative controls in order to verify the specificity of the reaction.

The detection was carried out with the PE-labelled anti-Fc conjugate.

The results are given in Table I below.

TABLE I

| | Cross match | | | |
|---|---|---|---|---|
| Recipient plasma/serum | Donor red blood cell | Expected result | Observed result | Transfusion danger |
| Anti-D serum No. 42 | Donor 0R2R2 (D) | + | + | incompatibility |
| | Donor 0rr (dd) | − | − | compatibility |
| Anti-c serum No. 62 | Donor 0R2R2 (cc) | + | + | incompatibility |
| | Donor 0R1R1 (CC) | − | − | compatibility |
| | Donor 0rr (cc) | + | + | incompatibility |
| Anti-K serum No. 70 | Donor 0R2R2 (kk) | − | − | compatibility |
| | Donor 0R1R1 (kk) | − | − | compatibility |
| | Donor 0rr (K+) | + | + | incompatibility |
| Anti-S serum No. 54 | Donor 0R2R2 (SS) | + | + | incompatibility |
| | Donor 0rr (ss) | − | − | compatibility |

The 12 donor plasmas make it possible to define an average negative value of less than 1100 RFI.

The sera which do not show incompatibility with the donor red blood cells produce values of less than 1000 RFI and sample value/average negative value ratios close to 1.

On the other hand, the sera which show incompatibility with the donor red blood cells give results of the order of 3000 to 27 000 RFI and sample value/average negative value ratios of the order of 3 to 27.

Moreover, the region-34 and -98 control beads give the expected signal levels, i.e., respectively, of the order of 8000 RFI and less than 1000 RFI.

This method makes it possible to clearly demonstrate a donor/recipient incompatibility, in blood systems as different as the Rhesus, Kell or MNS system.

Example 4

Reverse ("Serum" or "Simonin") ABO Grouping Test

The objective of this analysis is to show the presence or absence, in a blood sample, of natural antibodies directed against the A and/or B blood group antigens. The result of this analysis, combined with that obtained in a direct test, makes it possible to establish the ABO group of the sample. The sample used in the reverse ABO grouping test may be a serum, plasma, or whole blood sample.

To demonstrate the possibility of carrying out this application within the technology of the invention, fluorescent beads are used to immobilize red blood cells of known ABO group via poly-L-lysine (PLL).

These beads are then brought into contact with the sample to be tested. The presence of antibodies is detected using an anti-human immunoglobulin antibody conjugate labelled with phycoerythrin (PE).

4.1. Material and Reagents

Fluorescent superparamagnetic beads having bead regions 38 and 71

The beads are stored at +4° C. in PBS buffer, pH 7.4.

Region-34 (internal standard beads (ISB)) and region-98 (blank beads (BB)) control fluorescent beads.

Poly-L-lysine (PLL) of molecular weight 70 000-130 000.

Anti-human IgM goat polyclonal antibody, 7374V (Bio-Rad) coupled to phycoerythrin (PE).

Group A and group B red blood cells from a sample taken on EDTA (EFS-Rungis).

Plasma and whole blood samples from a sample taken on EDTA (EFS-Rungis).

Diluting medium sold under the name "ScanLiss" code 86442 by the company Bio-Rad.

Coating liquid or buffer (10 mM sodium phosphate, 150 mM NaCl, 0.1% (v/v) proclin).

Bovine serum albumin (BSA) (Millipore).

PBS buffer, pH 7.4 (7 mM sodium phosphate, 2.7 mM KCl, 136 mM NaCl).

4.2. Protocol 4.2.1. Sensitization of Beads with PLL

Region-38 and region-71 neutral beads are incubated with 50 µg/ml of PLL in PBS, pH 7.4, for 18 hours at ambient temperature and with agitation. At the end of this step, the beads are washed with PBS buffer, pH 7.4, and then used to immobilize red blood cells.

4.2.2. Immobilization of the Red Blood Cells from the Samples on the Beads

The bead-red blood cell reagents are prepared by mixing the PLL-coated beads and the red blood cells diluted in Scan- Liss, in a red blood cell number to bead number ratio equal to 100. The incubation is carried out with agitation for 5 minutes at ambient temperature. Each bead region is used to immobilize a single type of red blood cell of known group. At the end of this step, the bead-PLL-red blood cell reagents are washed several times with distilled water. The bead-red blood cell reagents thus prepared are stored in PBS-BSA 10 g/l, pH 7.4, at +4° C.

The principle of immobilization of the red blood cells on the beads by means of PLL is summarized in FIG. 4.

The attachment of the red blood cells by means of the PLL is sufficiently solid to prevent them from detaching during the tests and analyses.

Before incubation with the antibodies being screened, the bead-PLL-red blood cell reagents are mixed with the region-34 (ISB) and region-98 (BB) control beads.

4.2.3. Reaction of the Bead-PLL-Red Blood Cell Reagents with the Antibodies

The sample to be tested is in this case either plasma or whole blood.

Twenty-five microlitres of bead-PLL-red blood cell reagent are mixed with 50 µl of sample to be tested and incubated for 15 minutes with agitation at 22° C.

After incubation, the complexes are washed several times with PBS buffer, pH 7.4.

4.2.4. Visualization of the Complexes Using the PE-Labelled Anti-Immunoglobulin

To detect the bead-PLL-red blood cell-antibody complexes, a PE-labelled antibody specific for human immunoglobulins is used. This antibody conjugate is used at a concentration of 5 µg/ml in PBS, pH 7.4, and is incubated with the complexes for 15 minutes at 37° C. with agitation. The complexes are then washed several times with PBS buffer, pH 7.4.

4.2.5. Flow Cytometry Measurements Using the "Bioplex 200" Apparatus from the Company Bio-Rad After the final wash and before the measurements, the complexes are taken up with 35 µl of the coating liquid. For each test, 25 µl of suspension are injected into the apparatus. The measurements are carried out by capture of 250 beads per region.

Various red blood cells of known group were used. For each red blood cell, negative controls were tested in order to verify the specificity of the reactions studied.

4.3. Example of Serum ABO Grouping Test in Samples of Plasma or Whole Blood Type The antibodies were detected using several beads of different regions sensitized with red blood cells of known and different groups. Region-38 beads coated with PLL were used to immobilize a group A red blood cell. Region-71 beads coated with PLL were used to immobilize a group B red blood cell.

The sensitized beads were mixed and then incubated with samples of plasma or whole blood type of group A, B, AB and O in order to test positive cases and negative cases; the negative cases make it possible to verify the specificity of the reaction for each bead-PLL-red blood cell reagent. The detection was carried out with the PE-labelled anti-human immunoglobulin conjugate.

The results are given in Table II below:

TABLE II

Serum ABO grouping test in samples of plasma or whole blood type

| Samples | | Reagents | |
|---|---|---|---|
| | | R38/GR A beads | R71/GR B beads |
| Group O | Plasma type | + | + |
| | Whole blood type | + | + |
| Group A | Plasma type | − | + |
| | Whole blood type | − | + |
| Group B | Plasma type | + | − |
| | Whole blood type | + | − |
| Group AB | Plasma type | − | − |
| | Whole blood type | − | − |

The samples which do not have antibodies against the red blood cell presented (bead-PLL-red blood cell reagent) show values of less than 1000 RFI.

On the other hand, for the samples which have antibodies against the red blood cell presented, the values obtained are much higher (from 2900 to 19 000 RFI).

These results are obtained for any type of sample, whether it is of plasma type or whole blood type.

Moreover, the region-34 and -98 control beads give the expected signal levels, i.e., respectively, of the order of 8000 RFI and less than 1000 RFI.

These results demonstrate the validity of the approach under consideration for carrying out the detection of natural antibodies in a sample of plasma or whole blood type.

Example 5

Grouping in Whole Blood

The possibility of carrying out red blood cell grouping with the technology of the invention was demonstrated in Example 1 by using fluorescent beads to immobilize the anti-red blood cell antibodies and by labelling the red blood cells of the sample with a fluorescent compound compatible with the wavelengths of the reporter laser of the "Bioplex 200" apparatus (Bio-Rad).

The objective of these tests is to show that the sample used in the grouping application may be a blood cell pellet sample but also a whole blood sample.

5.1—Material and Reagents

Fluorescent superparamagnetic beads having bead regions 36 and 52

The beads are stored at +4° C. in PBS buffer, pH 7.4.

Region-34 (internal standard beads (ISB)) and region-98 (blank beads (BB)) control fluorescent beads.

Anti-murine IgG goat polyclonal antibody, code 115-005-164 (Jackson 1 mm. Lab.)
  Anti-murine IgM goat polyclonal antibody, code 115-005-020 (Jackson 1 mm. Lab.)
  Anti-B monoclonal IgG antibody, clone X9 (Bio-Rad).
  Anti-A monoclonal IgM antibody, clone 15750F7 (Bio-Rad).
  Samples of blood cell pellet and of whole blood taken on EDTA (EFS-Rungis).
  PKH26 cell labelling kit (Sigma).
  Diluting media sold under the names "ScanLiss" code 86442 and "Stabiliss" code 86550 by the company Bio-Rad.
  Coating liquid or buffer (10 mM sodium phosphate, 150 mM NaCl, 0.1% (v/v) proclin.

Bovine serum albumin (BSA) (Millipore).
PBS buffer, pH 7.4 (7 mM sodium phosphate, 2.7 mM KCl, 136 mM NaCl).

5.2–Protocol 5.2.1. Sensitization of Beads with Antibodies Directed Against Blood Groups The principle of immobilization of the antibodies at the surface of the beads is summarized in FIG. 2.

Region-36 beads were used to covalently immobilize the anti-murine IgG.

Region-52 fluorescent beads were used to covalently immobilize the anti-murine IgM. The carboxylic groups present at the surface of the beads were activated according to a technique involving a hydroxysuccinimide and a carbodiimide.

The proteins could thus be immobilized via their amine groups.

The beads thus prepared are stored at +4° C. at a concentration of 3 mg/ml in PBS, pH 7.4, containing 10% (w/v) of BSA, 0.5% (v/v) of Tween 20 and 0.09% (w/v) of sodium azide.

The beads carrying the immobilized anti-murine IgG can be sensitized with the anti-B antibody. The beads carrying the immobilized anti-murine IgM can be sensitized with the anti-A antibody. The anti-immunoglobulins in fact allow binding of immunoglobulins via their Fc fragment. The anti-red blood cell antibodies are therefore immobilized noncovalently on the beads using this principle. Each bead region is sensitized with an antibody of different specificity. The anti-immunoglobulins chosen have a high affinity for murine immunoglobulins, thus allowing this binding to be stable over time.

The nonpurified anti-A and the nonpurified anti-B are used at the respective final concentrations of 165 and 640 µg/ml with beads functionalized with the anti-Fc at 40 µg/mg.

The sensitization with the anti-red blood cell antibodies is carried out in PBS, pH 7.4, with agitation at 37° C. for one hour.

After sensitization, the beads are washed several times with PBS buffer, pH 7.4, and then stored at +4° C. in StabiLiss.

Before incubation with the red blood cells, the beads sensitized with the anti-red blood cell antibodies are mixed with region-34 control beads (ISB) and region-98 control beads (BB).

5.2.2. Labelling of Red Blood Cells

The labelling of the red blood cells is carried out as in Example 1 using PKH26 (FIG. 3).

The labelling of the red blood cells with PKH26 is carried out using the protocol recommended by the manufacturer. The red blood cells thus labelled are either diluted directly in the Stabiliss buffer in the case of a blood cell pellet sample, or diluted to 40% (v/v) in their plasma before they are diluted in StabiLiss in the case of a whole blood sample. The diluted samples are stored in the dark at +4° C.

5.2.3. Incubation of Anti-Red Blood Cell Antibody-Beads and Red Blood Cells

The sample to be tested is in this case either a blood cell pellet or whole blood, with a red blood cell content which goes up to 40%.

The sensitized beads are mixed with the samples in order to obtain a red blood cell number/sensitized bead number ratio of 50 to 100. The incubation of the mixture is carried out in StabiLiss for 15 minutes with agitation at 22° C.

After incubation, the bead-red cell complexes are washed several times with distilled water.

5.2.4. Flow Cytometry Measurements Using the "Bioplex 200" Apparatus from the Company Bio-Rad After the final wash and before the measurements, the complexes are taken up with 35 µl of the coating liquid. For each test, 25 µl of suspension are injected into the apparatus. The measurements are carried out by capture of 250 beads per region.

For each sensitized bead, negative samples were tested in order to verify the specificity of the reactions studied.

Figure 11:
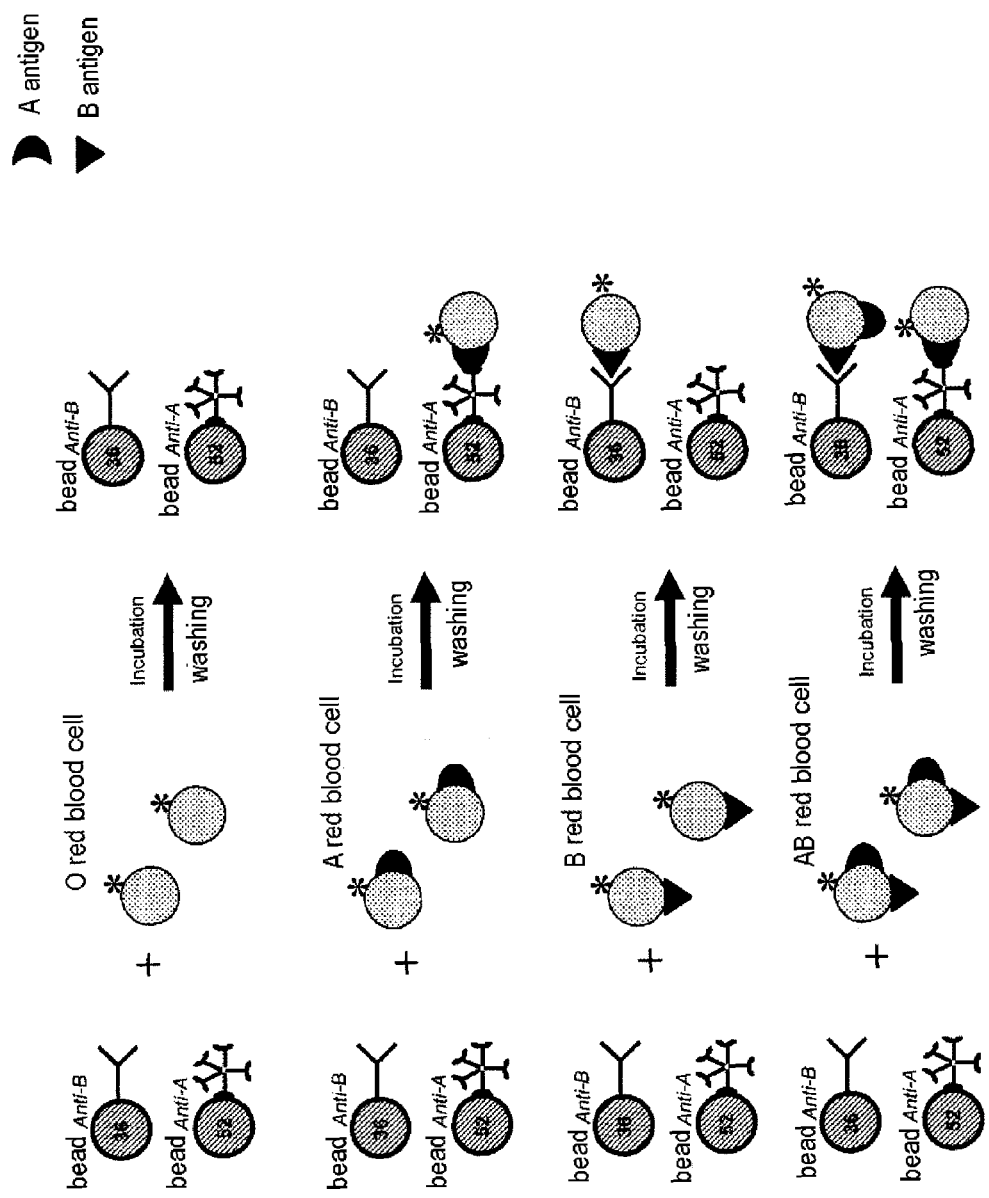
FIG. 11 is a scheme illustrating multiplex grouping on samples of blood cell pellet or whole blood type.

5.3—Example of Multiplex Grouping on Samples of Blood Cell Pellet or Whole Blood Type The principle of the multiplexed grouping is summarized in FIG. 11. Region-36 beads sensitized with an anti-B antibody were mixed with region-52 beads sensitized with an anti-A antibody, with ISB 34 control beads and with BB 98 control beads.

This mixture of beads was incubated with samples of group O, A, B or AB, with a red blood cell number/sensitized bead number ratio of approximately 50.

The results are given in Table III below.

TABLE III

Multiplex grouping on samples of blood cell pellet or whole blood type

| | | Multiplex reagent | |
|---|---|---|---|
| | Samples | R52/Anti-A beads | R36/Anti-B beads |
| Group O | Blood cell pellet type | – | – |
| | Whole blood type | – | – |
| Group A | Blood cell pellet type | + | – |
| | Whole blood type | + | – |
| Group B | Blood cell pellet type | – | + |
| | Whole blood type | – | + |
| Group AB | Blood cell pellet type | + | + |
| | Whole blood type | + | + |

With the bead-anti-A reagent, the A-positive red blood cells produce signals of greater than 30 000 RFI, whereas the A-negative red blood cells give signals of 30 to 50 RFI. Similarly, with the bead-anti-B reagent, the B-positive red blood cells produce signals of greater than 30 000 RFI, whereas the B-negative B red blood cells give signals of 30 to 50 RFI.

These results are obtained for any type of sample, whether in the form of a blood cell pellet or in the form of whole blood.

Moreover, the region-34 and -98 control beads give the expected signal levels, i.e., respectively, of the order of 7500 RFI and less than 1000 RFI.

These results demonstrate the validity of the approach under consideration for carrying out the grouping in a sample of blood cell pellet or whole blood type.

Example 6

Atypical Antibody Screen and Identification Multiplexed Methodology with an Identification Panel of 10 Red Blood Cells The atypical antibody screen (AAS) is generally carried out in 2 steps: a first step carried out on a restricted panel of red blood cells, the aim of which is to indicate the presence or absence of atypical antibodies directed against blood group antigens without enabling them to be identified. When the presence of antibodies is detected, a second step is carried out in order to identify the specificity of the antibody or antibodies in question. This second step is carried out with a panel of 10 red blood cells or more depending on the complexity of the mixture of antibodies to be identified. A sample volume of at least 350 µl is required in order to carry out the two steps. The objective of this test is to show the feasibility of identifying the atypical antibodies possibly present in a sample directly in a single test and with a single test sample of plasma or serum to be tested (50 to 100 μl).

To demonstrate the feasibility of this application in the technology of the invention, fluorescent beads are used to immobilize the red blood cells of the panel via poly-L-lysine (PLL). There are as many bead regions as there are red blood cells in the panel, each bead region being used to immobilize a single type of red blood cell of the panel, having a known and different phenotype.

These beads are mixed and brought into contact with the sample to be tested, and the atypical antibodies are detected using an anti-human immunoglobulin antibody conjugate labelled with phycoerythrin (PE).

6.1—Material and Reagents

Fluorescent superparamagnetic beads having bead regions 6, 8, 36, 38, 52, 71, 79, 81, 94 and 96

The beads are stored at +4° C. in PBS buffer, pH 7.4.

Region-34 (internal standard beads ISB)) and region-98 (blank beads (BB)) control fluorescent beads.

Poly-L-lysine (PLL) of molecular weight 70 000-130 000.

Anti-human immunoglobulin mouse IgG monoclonal antibody, clone 125A15 (Bio-Rad) coupled to phycoerythrin (PE).

Phenotyped blood cell concentrates stored in SAG-MAN medium (EFS Nord de France).

Diluting medium sold under the name "ScanLiss" code 86442 by the company Bio-Rad.

Coating liquid or buffer (10 mM sodium phosphate, 150 mM NaCl, 0.1% (v/v) proclin).

Bovine serum albumin (BSA) (Millipore).

PBS buffer, pH 7.4 (7 mM sodium phosphate, 2.7 mM KCl, 136 mM NaCl).

Plasma sample taken on EDTA (EFS-Rungis).

Serum samples having atypical blood group antibodies of the following specificities: anti-D, anti-Jka, anti-Kell.

6.2—Protocol 6.2.1. Sensitization of Beads with PLL

The bead-PLL reagent is prepared by incubating region-6, -8, -36, -38, -52, -71, -79, -81, -94 or -96 neutral beads with 50 μg/ml of PLL in PBS, pH 7.4, for 18 hours at ambient temperature and with agitation. At the end of this step, the bead-PLL complex is washed with PBS buffer, pH 7.4, and then used to immobilize the donor red blood cells.

6.2.2. Immobilization of Red Blood Cells on the Beads

The bead-PLL-red blood cell reagents are prepared by mixing the PLL-coated beads and the red blood cells of the panel, diluted in ScanLiss, in a red blood cell number/bead number ratio equal to 100. The incubation is carried out with agitation for 5 minutes at ambient temperature. Ten red blood cells of known and different phenotype are used to constitute an identification panel. Each bead region is used to immobilize a single type of red blood cell from this panel.

After incubation, the bead-PLL-red blood cell reagents are washed several times with distilled water and then taken up in PBS-BSA 10 g/l, pH 7.4.

The principle of the immobilization of the red blood cells on the beads by means of PLL is summarized in FIG. 4.

The attachment of the red blood cells by means of the PLL is sufficiently solid to prevent them from detaching during the remainder of the test and the analyses.

The bead-PLL-red blood cell reagents thus prepared and the region-34 and region-98 control beads are mixed and then incubated with the samples to be tested.

6.2.3. Reaction of the Bead-PLL-Red Blood Cell Reagents with the Antibodies

The mixture of the bead-PLL-red blood cell reagents prepared individually from different red blood cells constitutes a panel for identifying the antibodies. 25 μl of this panel are mixed with 100 μl of sample to be tested (plasma or serum) and incubated for 15 minutes with agitation at 37° C.

After incubation, the complexes are washed several times with PBS buffer, pH 7.4.

6.2.4. Visualization of the Complexes Using the PE-Labelled Anti-Fc

To detect the bead-PLL-red blood cell-antibody complexes, a PE-labelled antibody specific for the human immunoglobulin Fc fragment is used. This antibody conjugate is used at a concentration of 1 μg/ml in PBS, pH 7.4, and is incubated with the complexes for 15 minutes at 37° C. with agitation. The complexes are then washed several times with PBS buffer, pH 7.4.

6.2.5. Flow Cytometry Measurements Using the "Bioplex 200" Apparatus from the Company Bio-Rad After the final wash and before the measurements, the complexes are taken up with 35 μl of the coating liquid. For each test, 25 μl of suspension are injected into the apparatus. The measurements are carried out by capture of the fluorescence signal from 250 beads per region.

6.3. Example of AAS for Identifying the Specificity of Atypical Antibodies in Plasma and/or Serum PLL-coated beads of different region were used to immobilize 10 red blood cells of known and different phenotypes: a red blood cell of phenotype D, kk, Jka+b+ was immobilized on region-6 beads, a red blood cell of phenotype D, Kk, Jka+b− on region-8 beads, a red blood cell of phenotype D, kk, Jka+b− on region-36 beads, a red blood cell of phenotype D, kk, Jka+b− on region-38 beads, a red blood cell of phenotype D, Kk, Jka+b+ on region-52 beads, a red blood cell of phenotype dd, Kk, Jka−b+ on region-71 beads, a red blood cell of phenotype dd, kk, Jka−b+ on region-79 beads, a red blood cell of phenotype dd, Kk, Jka+b+ on region-81 beads, a red blood cell of phenotype dd, kk, Jka−b+ on region-94 beads, and a red blood cell of phenotype dd, kk, Jka+b+ on region-96 beads.

The sensitized beads were mixed and then incubated with various sera having atypical blood group antibodies of various specificities (anti-D, anti-Kell, anti-Jka) or mixtures of these sera so as to reproduce an antibody mixture. These sera represent positive samples that may potentially have antibodies directed against the red blood cells of the panel. They were chosen in order to detect blood antigen systems that are different in terms of structure and of antigen presentation, and also in terms of antigen density on the red blood cell.

Eight donor plasmas having no atypical antibody were also tested and used as negative controls in order to verify the specificity of the reaction.

The detection was carried out with the PE-labelled anti-human Fc conjugate.

The results are given in Table IV below.

The 8 donor plasmas make it possible to define an average negative value of less than 1100 RFI.

The sera which do not have antibodies directed against the red blood cells of the panel produce values of less than 1000 RFI.

On the other hand, the sera which have antibodies directed against the antigens carried by the red blood cells of the panel give results of the order of 2000 to 31 000 RFI and sample value/average negative value ratios of the order of 15 to 207.

Moreover, the region-34 and -98 control beads give the expected signal levels, i.e., respectively, of the order of 8000 RFI and less than or equal to 1000 RFI.

This method makes it possible to clearly demonstrate the presence of atypical antibodies and to identify their specificity in blood systems as different as the Rhesus, Kell or Kidd systems.

7.1—Material and Reagents

Fluorescent superparamagnetic beads having bead regions 6, 56, 71, 81 and 94

The beads are stored at +4° C. in PBS buffer, pH 7.4.

Region-34 (internal standard beads (ISB)) and region-98 (blank beads (BB)) control fluorescent beads.

TABLE IV

AAS for identifying the specificity of atypical antibodies in plasma and/or serum

| | | Samples | | | | | | | | | | | | |
|---|---|---|---|---|---|---|---|---|---|---|---|---|---|---|
| Reagent | | 8 negative plasmas | | Anti-D serum No. 42 | | Anti-Jka serum No. 65 | | Anti-Kell serum No. 70 | | Anti-D (No. 42) + anti-JKa (No. 65) sera | | Anti-D (No. 42) + anti-Kell (No. 70) sera | | Anti-JKa (No. 65) + anti-Kell (No. 70) sera |
| (beads-PLL-red corpuscle mixture) | | expected result | observed result | expected result | observed result | expected result | observed result | expected result | observed result | expected result | observed result | expected result | observed result | expected result | observed result |
| Bead region | Red blood phneotype | | | | | | | | | | | | | |
| Region 6 | D, kk, Jka+b+ | − | − | + | + | + | + | − | − | + | + | + | + | + | + |
| Region 8 | D, Kk, Jka+b− | − | − | + | + | + | + | + | + | + | + | + | + | + | + |
| Region 36 | D, kk, Jka+b− | − | − | + | + | + | + | − | − | + | + | + | + | + | + |
| Region 38 | D, kk, Jka+b− | − | − | + | + | + | + | − | − | + | + | + | + | + | + |
| Region 52 | D, Kk, Jka+b+ | − | − | + | + | + | + | + | + | + | + | + | + | + | + |
| Region 71 | dd, Kk, Jka−b+ | − | − | − | − | − | − | + | + | − | − | + | + | + | + |
| Region 79 | dd, kk, Jka−b+ | − | − | − | − | − | − | − | − | − | − | − | − | − | − |
| Region 81 | dd, kk, Jka+b+ | − | − | − | − | + | + | + | + | + | + | + | + | + | + |
| Region 94 | dd, kk, Jka−b+ | − | − | − | − | − | − | − | − | − | − | − | − | − | − |
| Region 96 | dd, kk, Jka+b+ | − | − | − | − | + | + | − | − | + | + | − | − | + | + |

Example 7

Blood Cell ABO Grouping Test and Serum ABO Grouping Test Carried Out Simultaneously, Ag-Ab Combo The possibility of carrying out the screening of antigens on the red blood cell with the technology of the invention was demonstrated in Examples 1 and 3, by using fluorescent beads to immobilize the anti-red blood cell antibodies and by labelling the red blood cells of the sample with a fluorescent compound compatible with the wavelengths of the reporter laser of the "Bioplex 200" apparatus (Bio-Rad). Similarly, the possibility of detecting the typical and atypical antibodies with the technology of the invention was demonstrated in Examples 2, 4 and 6, by using fluorescent beads to immobilize the red blood cells via poly-L-lysine (PLL) and by detecting the presence of antibodies in the sample against the red blood cells presented, using an anti-human immunoglobulin antibody conjugate labelled with phycoerythrin (PE). The objective of these tests is to show that the technology of the invention makes it possible to screen for antigens and screen for antibodies in one and the same receptacle.

To demonstrate the feasibility of this double determination, a multiplex test was carried out, combining fluorescent beads for detecting the A and/or B antigens carried by the red blood cells of the sample to be tested and fluorescent beads bound to red blood cells of known ABO group, for detecting the anti-A and/or anti-B antibodies present in the sample to be tested. The sample to be tested is a sample of whole blood type. The two visualization systems described above are used: labelling of the red blood cells of the sample with a fluorescent compound for detecting the antigens at the surface of the red blood cell, and the use of a PE-labelled anti-human immunoglobulin secondary antibody for detecting antibodies in the plasma of the sample to be tested.

Anti-murine IgG goat polyclonal antibody, code 115-005-164 (Jackson 1 mm. Lab.)

Anti-murine IgM goat polyclonal antibody, code 115-005-020 (Jackson 1 mm. Lab.)

Anti-B monoclonal IgG antibody, clone X9 (Bio-Rad).

Anti-A monoclonal IgM antibody, clone 15750F7 (Bio-Rad).

Anti-human IgM goat polyclonal antibody, code 709-116-073 (Jackson 1 mm. Lab.) coupled to phycoerythrin (PE).

PKH26 cell labelling kit (Sigma).

Poly-L-lysine (PLL) of molecular weight 70 000-130 000.

Whole blood samples taken on EDTA (EFS-Rungis).

Diluting media sold under the names "ScanLiss" code 86442 and "Stabiliss" code 86550 by the company Bio-Rad.

Coating liquid or buffer (10 mM sodium phosphate, 150 mM NaCl, 0.1% (v/v) proclin).

Bovine serum albumin (BSA) (Millipore).

PBS buffer, pH 7.4 (7 mM sodium phosphate, 2.7 mM KCl, 136 mM NaCl).

7.2—Protocol 7.2.1. Preparation of Reagents 7.2.1.1 Preparation of Reagents for Detecting Antigens: Sensitization of Beads with Antibodies Directed Against the Blood Groups The principle of the immobilization of the antibodies at the surface of the beads is summarized in FIG. 2.

Region-6 beads were used to covalently immobilize the anti-murine IgG.

Region-56 fluorescent beads were used to covalently immobilize the anti-murine IgM. The carboxylic groups present at the surface of the beads were activated according to a technique involving a hydroxysuccinimide and a carbodiimide.

The proteins could thus be immobilized via their amine groups.

The beads thus prepared are stored at +4° C. at a concentration of 3 mg/ml in PBS, pH 7.4, containing 10% (w/v) of BSA, 0.5% (v/v) of Tween 20 and 0.09% (w/v) of sodium azide.

The beads carrying the immobilized anti-murine IgG can be sensitized with the anti-B antibody. The beads carrying the immobilized anti-murine IgM can be sensitized with the anti-A antibody. The anti-red blood cell antibodies are therefore noncovalently immobilized on the beads using this principle. Each bead region is sensitized with an antibody of different specificity. The anti-immunoglobulins chosen allow stable binding over time.

The nonpurified anti-A and the nonpurified anti-B are used at the respective final concentrations of 165 and 640 µg/ml.

The sensitization with the anti-red blood cell antibodies is carried out in PBS, pH 7.4, with agitation at 37° C. for one hour.

After sensitization, the beads are washed several times with PBS buffer, pH 7.4, and then stored at +4° C. in PBS-BSA 10 g/l, pH 7.4.

7.2.1.2 Preparation of Reagents for Detecting Antibodies: Sensitization of Beads with PLL and Immobilization of Red Blood Cells of Known Group and Known Phenotype Region-71, region-81 and region-94 neutral beads are incubated with 50 µg/ml of PLL in PBS, pH 7.4, for 18 hours at ambient temperature and with agitation. At the end of this step, the beads are washed with PBS buffer, pH 7.4, and then used to immobilize the red blood cells.

The bead-red blood cell reagents are prepared by mixing the PLL-coated beads and the red blood cells diluted in Scan-Liss, in a red blood cell number to bead number ratio equal to 100. The incubation is carried out with agitation for 5 minutes at ambient temperature. Each bead region is used to immobilize a single type of red blood cell of known group. At the end of this step, the bead-PLL-red blood cell reagents are washed several times with distilled water. The bead-red blood cell reagents thus prepared are stored in PBS-BSA 10 g/l, pH 7.4, at +4° C.

The principle of the immobilization of the red blood cells on the beads by means of PLL is summarized in FIG. 4.

The attachment of the red blood cells by means of the PLL is sufficiently solid to prevent them from detaching during the tests and analyses.

7.2.2. Labelling of the Red Blood Cells of the Samples to be Tested

The labelling of the red blood cells is carried out as in Example 1 using PKH26 (FIG. 3).

The labelling of the red blood cells with PKH26 is carried out using the protocol recommended by the manufacturer. The red blood cells thus labelled are diluted to 40% (v/v) in their plasma.

7.2.3. Incubation of the Samples to be Tested with the Blood Group Antibody-Beads and the Red Blood Cell-Beads The sample to be tested is whole blood.

Fifty microlitres of sample to be tested are mixed with 25 µl of beads sensitized with the red blood cells of known phenotype (bead-PLL-red blood cell reagents) and incubated for 10 minutes with agitation at 22° C.

Twenty-five microlitres of beads sensitized with the anti-red blood cell antibodies (bead-anti-red blood cell antibody reagents) are then added and incubated for 5 minutes with agitation at 22° C.

After incubation, the reagents are washed several times with PBS buffer.

7.2.4. Detection of Positive Complexes

The detection of the red blood cells bound by the bead-anti-red blood cell antibody reagents (bead-antibody-red blood cell complexes) is provided by the prior labelling of the red blood cells of the sample.

To detect the binding of the antibodies of the sample to the bead-PLL-red blood cell reagents (bead-PLL-red blood cell-antibody complexes), a PE-labelled antibody specific for human immunoglobulins is used. This antibody conjugate is used at a concentration of 5 µg/ml in PBS, pH 7.4, and is incubated with the complexes for 15 minutes at 37° C. with agitation. The complexes are then washed several times with PBS buffer, pH 7.4.

7.2.5. Flow Cytometry Measurements Using the "Bioplex 200" Apparatus from the Company Bio-Rad After the final wash and before the measurements, the complexes are taken up with 35 µl of the coating liquid. For each test, 25 µl of suspension are injected into the apparatus. The measurements are carried out by capture of 250 beads per region.

For each sensitized bead, negative samples were tested in order to verify the specificity of the reactions studied.

7.3—Example of Multiplex Direct and Indirect ABO Grouping

Region-94 beads coated with PLL were used to immobilize a group A1 red blood cell, region-71 beads coated with PLL were used to immobilize a group B red blood cell and region-81 beads coated with PLL were used to immobilize a group O red blood cell. These beads sensitized with red blood cells of known phenotype were mixed.

Region-6 beads sensitized with an anti-B antibody were mixed with region-56 beads sensitized with an anti-A antibody, with ISB 34 control beads and with BB 98 control beads.

Samples of whole blood of group A, B, AB and O were tested.

The red blood cells of the samples were labelled beforehand so as to allow them to be detected if they are bound by the anti-red blood cell antibody-beads. The antibodies of the samples bound to the red blood cell-beads were detected with a PE-labelled anti-human immunoglobulin conjugate.

The results are given in Table V below:

TABLE V

Multiplex direct and indirect ABO grouping

| | Multiplex test | | | | |
|---|---|---|---|---|---|
| | Antigen detection | | Antibody detection | | |
| Samples | R56/Anti-A beads | R6/Anti-B beads | R94/GR A1 beads | R71/GR B beads | R81/GR O beads |
| Group O | − | − | + | + | − |
| Group A | + | − | − | + | − |
| Group B | − | + | + | − | − |
| Group AB | + | + | − | − | − |

Result of the Blood Cell Test (Antigen Detection):

The bead-anti-A and bead-anti-B reagents react respectively with the A positive red blood cells and B positive red blood cells: the positive samples produce positive signals of greater than 28 000 RFI, whereas the negative samples give much lower signals, of 1800 to 8300 RFI.

Results of the Serum Test (Antibody Detection):

The samples which do not contain antibodies against the red blood cell presented produce values of less than 1800 RFI, with an average negative value of 1020 RFI.

The samples which have antibodies against the red blood cell presented by the bead-PLL-A1 red blood cell and bead-PLL-B red blood cell reagents give positive signals of 3000 to 8200 RFI with sample value versus average negative value ratios of the order of 3 to 8.

Moreover, the region-34 and region-98 control beads give the expected signal levels, i.e., respectively, of the order of 8000 RFI and less than 1400 RFI.

These results demonstrate the feasibility of carrying out the multiplexed detection of antigens and antibodies, in one and the same receptacle and using a single test sample of a whole blood sample.

The invention claimed is:

1. An in vitro method for identifying a plurality of anti-erythrocyte antibodies in a biological sample, by
   (i) bringing said biological sample into contact, in a single test receptacle, or in several separate test receptacles, with groups of distinguishable beads, each group of distinguishable beads carrying (1) erythrocytes carrying antigenic molecules to which said anti-erythrocyte antibodies bind or (2) erythrocyte membrane fragments carrying antigenic molecules to which said anti-erythrocyte antibodies bind under conditions which allow the antibodies or activated serum complement fractions present in the sample to bind to said antigenic molecules on the erythrocytes or the erythrocyte membrane fragments, without agglutination,
   (ii) eliminating the antibodies or activated serum complement fractions which have not bound to said erythrocytes or to said erythrocyte membrane fragments,
   (iii) labelling the bound antibodies and/or the bound activated serum complement fractions, and
   (iv) analyzing the mixture so as to identify the group of beads having bound the labelled antibodies or the labelled activated serum complement fractions, thereby allowing the identification of the anti-erythrocyte antibodies.

2. The method according to claim 1, wherein the anti-erythrocyte antibodies are directed against antigenic molecules selected from the group consisting of erythrocyte membrane antigens constituting the blood groups, activated serum complement fractions carried by the erythrocytes, and antibodies present at the surface of the sensitized erythrocytes.

3. The method according to claim 1, wherein the method comprises haemolysis of said erythrocytes prior to said analysis of the mixture, said haemolysis resulting in degradation of haemoglobin within said erythrocytes.

4. The method according to claim 1, wherein the distinguishable beads are superparamagnetic or magnetic or magnetizable beads.

5. The method according to claim 1, wherein the distinguishable beads emit luminescent or fluorescent signals.

6. The method according to claim 1, wherein the antibodies are labelled by bringing into contact with an anti-human globulin antibody carrying a fluorescent, luminescent or radioactive label.

7. The method according to claim 1, wherein the activated serum complement fractions are labelled by bringing into contact with an anti-serum complement fraction antibody carrying a fluorescent, luminescent or radioactive label.

8. The method according to claim 1, comprising identifying atypical antibodies.

9. The method according to claim 1, wherein the biological sample is selected from the group consisting of whole blood, plasma, serum and a blood cell pellet.

10. The method according to claim 1, wherein the biological sample originates from an individual having erythrocytes sensitized in vivo by antibodies, and/or coated with the serum complement fraction.

11. The method according to claim 1, wherein the isotype of the immunoglobulins present at the surface of the erythrocytes and/or in a biological fluid originating from said individual is determined.

12. The method according to claim 1, also comprising the quantification of the antibodies identified.

13. The method according to claim 1, wherein the analysis of the mixture is carried out by flow cytometry.

14. The method of claim 1, wherein the beads carry erythrocytes.

15. The method of claim 1, wherein the beads carry erythrocyte membrane fragments.

16. A method for cross matching erythrocytes that must be transfused into a patient, comprising:
   (i) simultaneously bringing a sample of serum or plasma from the patient into contact, in a single test receptacle, with groups of distinguishable beads carrying erythrocytes carrying antigenic molecules to which anti-erythrocyte antibodies bind for transfusion into said patient, under conditions which allow antibodies present in the sample to bind to the antigenic molecules carried by said erythrocytes, without agglutination,
   (ii) eliminating the antibodies which have not bound to antigenic molecules carried by said erythrocytes carried on said distinguishable beads,
   (iii) labelling the antibodies which are bound to the antigenic molecules carried by said erythrocytes bound to said distinguishable beads, and
   (iv) analyzing the mixture so as to determine whether a group of beads has antibodies from said sample bound to antigenic molecules carried by said erythrocytes, the binding of antibodies to a group of beads signifying that the erythrocytes for transfusion into said patient are not a perfect match.

17. A set of reagents comprising a group of distinguishable beads, said group of distinguishable beads being detectably distinguishable according to a physicochemical property selected from the group consisting of size, density, roughness, absorbance, fluorescence, luminescence, paramagnetism, magnetism and ability to be magnetized, and carrying (1) erythrocytes carrying antigenic molecules or (2) an erythrocyte membrane fragment carrying antigenic molecules to which anti-erythrocyte antibodies bind.

18. An in vitro method for identifying antigenic molecules carried by erythrocytes and anti-erythrocyte antibodies of an individual, comprising:
   a) identifying a plurality of antigenic molecules carried by erythrocytes in a biological sample, by
      (i) bringing said sample containing erythrocytes into contact, in a single test receptacle, or in several separate test receptacles, with groups of distinguishable beads, each group of distinguishable beads carrying a given antibody, specific for an antigenic molecule carried by erythrocytes, which differs from one group of beads to the other, under conditions which allow the erythrocytes to bind to the antibodies, without agglutination, said erythrocytes being labelled before or after they have been brought into contact with said groups of beads,
      (ii) eliminating the erythrocytes which have not bound to said antibodies, and (iii) analyzing the mixture so as to identify the group of beads having bound the labelled erythrocytes, thereby allowing the identification of the antigens carried by the erythrocytes detected; and b) identifying a plurality of anti-erythrocyte antibodies in a biological sample, by
   (i) bringing said biological sample into contact, in a single test receptacle, or in several separate test receptacles, with groups of distinguishable beads, each group of distinguishable beads carrying (1) erythrocytes carrying antigenic molecules or (2) erythrocyte membrane fragments carrying antigenic molecules, under conditions which allow the antibodies or activated serum complement fractions present in the sample to bind to said antigenic molecules on said erythrocytes or said erythrocyte membrane fragments, without agglutination,
   (ii) eliminating the antibodies or activated serum complement fractions which have not bound to antigenic molecules on said erythrocytes or said erythrocyte membrane fragments,
   (iii) labelling the bound antibodies and/or the bound activated serum complement fractions, and
   (iv) analyzing the mixture so as to identify the group of beads having bound the labelled antibodies or the labelled activated serum complement fractions, thereby allowing the identification of the anti-erythrocyte antibodies present in said biological sample that specifically bind to said antigenic molecules carried by said erythrocytes or said erythrocyte membrane fragments.

19. The method according to claim 18, wherein the antigenic molecules carried by the erythrocytes are selected from the group consisting of erythrocyte membrane antigens constituting the blood groups, activated serum complement fractions carried by the erythrocytes, and antibodies present at the surface of the sensitized erythrocytes.

20. The method according to claim 18, wherein the identifying of the antigens according to a) and the identifying of the antibodies according to b) are carried out simultaneously and in the same receptacle.

21. The method according to claim 18, wherein the method comprises haemolysis of said erythrocytes prior to said analysis of the mixture, said haemolysis resulting in degradation of haemoglobin within said erythrocytes.

22. The method according to claim 18, wherein the distinguishable beads are superparamagnetic or magnetic or magnetizable beads.

23. The method according to claim 18, wherein the distinguishable beads emit luminescent or fluorescent signals.

24. The method according to claim 18, wherein the erythrocytes according to step a) are labelled with a fluorescent compound.

25. The method according to claim 18, wherein the antibodies of step b) are labelled by bringing into contact with an anti-human globulin antibody carrying a fluorescent, luminescent or radioactive label.

26. The method according to claim 18, wherein the activated serum complement fractions of step b) are labelled by bringing into contact with an anti-serum complement fraction antibody carrying a fluorescent, luminescent or radioactive label.

27. The method according to claim 18, comprising identifying a plurality of anti-erythrocyte antibodies of step b), wherein the antibodies are atypical antibodies.

28. The method according to claim 18, wherein the biological sample is selected from the group consisting of whole blood, plasma, serum and a blood cell pellet.

29. The method according to claim 18, wherein the biological sample originates from an individual having erythrocytes sensitized in vivo by antibodies, and/or coated with the serum complement fraction.

30. The method according to claim 18, wherein the isotype of the immunoglobulins present at the surface of the erythrocytes and/or in a biological fluid originating from said individual is determined.

31. The method according to claim 18, also comprising the quantification of the antibodies identified in step b).

32. The method according to claim 18, wherein the analysis of the mixture is carried out by flow cytometry.

33. The method of claim 18, wherein the beads carry erythrocytes.

34. The method of claim 18, wherein the beads carry erythrocyte membrane fragments.

35. A set of reagents comprising groups of distinguishable beads, each group of distinguishable beads being detectably distinguishable according to a physicochemical property selected from the group consisting of size, density, particle size, roughness, absorbance, fluorescence, luminescence, paramagnetism, magnetism, and ability to be magnetized, and belonging to at least two different groups, one of the groups carrying a capture antibody specific for an antigenic molecule carried by erythrocytes, and the other group carrying (1) erythrocytes carrying antigenic molecules or (2) erythrocyte membrane fragments carrying antigenic molecules.

* * * * *

UNITED STATES PATENT AND TRADEMARK OFFICE
CERTIFICATE OF CORRECTION

| | | |
|---|---|---|
| PATENT NO. | : 8,580,530 B2 | Page 1 of 1 |
| APPLICATION NO. | : 12/601825 | |
| DATED | : November 12, 2013 | |
| INVENTOR(S) | : Frederic Buffiere et al. | |

It is certified that error appears in the above-identified patent and that said Letters Patent is hereby corrected as shown below:

In The Specification

<u>Column 13,</u>
Line 63, "single anti en" should read --single antigen--.

Signed and Sealed this
Tenth Day of February, 2015

Michelle K. Lee
*Deputy Director of the United States Patent and Trademark Office*